United States Patent
Aeschlimann et al.

(10) Patent No.: US 7,335,205 B2
(45) Date of Patent: *Feb. 26, 2008

(54) IMPLANTS, DEVICE AND METHOD FOR JOINING TISSUE PARTS

(75) Inventors: Marcel Aeschlimann, Ligerz (CH); Laurent Torriani, Biel (CH); Antonino Lanci, Bern (CH); Jörg Mayer, Niederlenz (CH)

(73) Assignee: Woodwelding AG, Zug (CH)

( * ) Notice: Subject to any disclaimer, the term of this patent is extended or adjusted under 35 U.S.C. 154(b) by 436 days.

This patent is subject to a terminal disclaimer.

(21) Appl. No.: 10/415,454

(22) PCT Filed: Mar. 4, 2002

(86) PCT No.: PCT/CH02/00132

§ 371 (c)(1), (2), (4) Date: Aug. 27, 2003

(87) PCT Pub. No.: WO02/069817

PCT Pub. Date: Sep. 12, 2002

(65) Prior Publication Data

US 2004/0030341 A1    Feb. 12, 2004

(30) Foreign Application Priority Data

Mar. 2, 2001   (CH)  .................................... 0387/01

(51) Int. Cl.
*A61B 17/56* (2006.01)
(52) U.S. Cl. ........................................ 606/72; 433/173
(58) Field of Classification Search ................. 606/72, 606/76, 77; 433/172, 173, 201.1
See application file for complete search history.

(56) References Cited

U.S. PATENT DOCUMENTS 772,029 A    10/1904    Clark (Continued)

FOREIGN PATENT DOCUMENTS

DE    2418198    4/1974

(Continued)

OTHER PUBLICATIONS

"Linear Vibration Welding of Non Metallic Components", Welding & Metal Fabrication, May 1989, pp. 152-154.

(Continued)

*Primary Examiner*—Eduardo C. Robert
*Assistant Examiner*—Michael J Araj
(74) *Attorney, Agent, or Firm*—Rankin, Hill, Porter & Clark LLP

(57) ABSTRACT

Implants (7) for forming a positive connection with human or animal parts include a material, such as thermoplastics and thixotropic materials, that can be liquefied by means of mechanical energy. The implants (7) are brought into contact with the tissue part, are subjected to the action of ultrasonic energy while being pressed against the tissue part. The liquefiable material liquefies and is pressed into openings or surface asperities of the tissue part so that, once solidified, the implant is positively joined thereto. The implantation involves the use of an implantation device that includes a generator (2), an oscillating element, and a resonator (6). The generator (2) causes the oscillating element to mechanically oscillate, and the element transmits the oscillations to the resonator (6). The resonator (6) is used to press the implant (7) against the tissue part to transmit oscillations to the implant (7).

124 Claims, 13 Drawing Sheets

U.S. PATENT DOCUMENTS

| | | | |
|---|---|---|---|
| 2,366,274 A | 1/1945 | Luth et al. | |
| 2,458,152 A | 1/1949 | Eakins | |
| 2,510,693 A | 6/1950 | Green | |
| 2,942,748 A | 6/1960 | Anderson | |
| 3,184,353 A | 5/1965 | Balamuth et al. | |
| 3,481,803 A | 12/1969 | Hewitt | |
| 3,499,222 A | 3/1970 | Linkow et al. | |
| 3,612,803 A | 10/1971 | Klass | |
| 3,723,215 A | 3/1973 | Kessler | |
| 3,919,775 A | 11/1975 | Malmin | |
| 4,032,803 A | 6/1977 | Durr et al. | |
| 4,100,954 A | 7/1978 | Muller et al. | |
| 4,130,751 A | 12/1978 | Gordon | |
| 4,248,232 A | 2/1981 | Engelbrecht et al. | |
| 4,328,108 A | 5/1982 | Deeken | |
| 4,360,343 A | 11/1982 | Hussein | |
| 4,482,795 A | 11/1984 | Hinden | |
| 4,525,147 A | 6/1985 | Pitz et al. | |
| 4,566,138 A | 1/1986 | Lewis et al. | |
| 4,675,972 A | 6/1987 | Bappert et al. | |
| 4,717,302 A | 1/1988 | Adams et al. | |
| 4,761,871 A | 8/1988 | O'Connor et al. | |
| 5,004,422 A | 4/1991 | Propper | |
| 5,019,083 A | 5/1991 | Klapper et al. | |
| 5,037,442 A | 8/1991 | Wintermantel et al. | |
| 5,125,442 A | 6/1992 | Hendrickson | |
| 5,163,960 A | 11/1992 | Bonutti | |
| 5,167,619 A | 12/1992 | Wuchinich | |
| 5,171,148 A | 12/1992 | Wasserman et al. | |
| 5,244,933 A | 9/1993 | Eidenbenz et al. | |
| 5,271,785 A | 12/1993 | Devine | |
| 5,308,205 A | 5/1994 | Lautenschlager | |
| 5,393,559 A | 2/1995 | Shoesmith et al. | |
| 5,413,578 A | 5/1995 | Zahedi | |
| 5,426,341 A | 6/1995 | Bory et al. | |
| 5,447,592 A | 9/1995 | Berce et al. | |
| 5,547,325 A | 8/1996 | Tucker et al. | |
| 5,562,450 A | 10/1996 | Gieloff et al. | |
| 5,589,015 A | 12/1996 | Fusco et al. | |
| 5,593,425 A | 1/1997 | Bonutti et al. | |
| 5,709,823 A | 1/1998 | Hahn | |
| 5,735,875 A | 4/1998 | Bonutti et al. | |
| 5,752,831 A | 5/1998 | Padros-Fradera | |
| 5,766,009 A | 6/1998 | Jeffcoat | |
| 5,772,359 A | 6/1998 | Marty | |
| 5,780,536 A | 7/1998 | Yokoyama et al. | |
| 5,785,476 A | 7/1998 | McDonnell | |
| 5,803,736 A | 9/1998 | Merritt, Jr. | |
| 5,840,154 A | 11/1998 | Wittmaier | |
| 5,871,514 A | 2/1999 | Wiklund et al. | |
| 5,871,515 A | 2/1999 | Wiklund et al. | |
| 5,897,578 A | 4/1999 | Wiklund et al. | |
| 5,919,215 A | 7/1999 | Wiklund et al. | |
| 5,938,633 A * | 8/1999 | Beaupre | 604/22 |
| 5,941,901 A | 8/1999 | Egan | |
| 5,964,764 A | 10/1999 | West, Jr. et al. | |
| 5,993,458 A | 11/1999 | Vaitekunas et al. | |
| 5,993,477 A | 11/1999 | Vaitekunas et al. | |
| 6,007,539 A | 12/1999 | Kirsch et al. | |
| 6,039,568 A | 3/2000 | Hinds | |
| 6,056,751 A | 5/2000 | Fenton, Jr. | |
| 6,059,817 A | 5/2000 | Bonutti et al. | |
| 6,068,482 A | 5/2000 | Snow | |
| 6,080,161 A | 6/2000 | Eaves, III et al. | |
| 6,099,313 A | 8/2000 | Dorken et al. | |
| 6,132,214 A | 10/2000 | Suhonen et al. | |
| 6,139,320 A | 10/2000 | Hahn | |
| 6,141,874 A | 11/2000 | Olsen | |
| 6,193,516 B1 | 2/2001 | Story | |
| 6,224,373 B1 | 5/2001 | Lee et al. | |
| 6,273,717 B1 | 8/2001 | Hahn et al. | |
| 6,332,885 B1 | 12/2001 | Martella | |
| 6,545,390 B1 | 4/2003 | Hahn et al. | |
| 6,592,609 B1 | 7/2003 | Bonutti | |
| 6,635,073 B2 | 10/2003 | Bonutti | |
| 6,913,666 B1 * | 7/2005 | Aeschlimann et al. | 156/73.1 |
| 6,921,264 B2 * | 7/2005 | Mayer et al. | 433/173 |
| 6,984,394 B2 * | 1/2006 | Menz et al. | 424/423 |
| 7,008,226 B2 * | 3/2006 | Mayer et al. | 433/173 |
| 2002/0044753 A1 | 4/2002 | Nagayama et al. | |
| 2002/0077662 A1 | 6/2002 | Bonutti et al. | |
| 2003/0118518 A1 | 6/2003 | Hahn et al. | |

FOREIGN PATENT DOCUMENTS

| | | |
|---|---|---|
| DE | 2655086 | 12/1976 |
| DE | 3045706 | 12/1980 |
| DE | 257797 | 2/1987 |
| DE | 3723643 A1 | 7/1987 |
| DE | 3828340 | 8/1988 |
| DE | 3919274 C1 | 6/1989 |
| DE | 9012044.2 | 8/1990 |
| DE | 9012548.7 | 9/1990 |
| DE | 4100636 A1 | 1/1991 |
| DE | 4209191 A1 | 3/1992 |
| DE | 4328108 | 8/1993 |
| DE | 0317757.7 | 11/1993 |
| DE | 19644333 A1 | 10/1996 |
| DE | 19735103 A1 | 8/1997 |
| DE | 19741087 | 9/1997 |
| DE | 19916158 A1 | 4/1999 |
| DE | 19916160 A1 | 4/1999 |
| DE | 19926899 A1 * | 12/2000 |
| DE | 20113692 U1 | 8/2001 |
| EP | 0268957 | 6/1988 |
| EP | 0415615 | 8/1990 |
| EP | 0451932 A1 | 4/1991 |
| EP | 0534078 A1 | 7/1992 |
| EP | 0 617 935 A2 | 10/1994 |
| EP | 1044655 | 3/2000 |
| EP | 1044656 A1 | 10/2000 |
| EP | 1184006 | 3/2002 |
| EP | 1199049 | 4/2002 |
| FR | 1164445 | 1/1957 |
| FR | 1407582 | 9/1964 |
| FR | 1495999 | 10/1966 |
| FR | 2205402 | 11/1973 |
| FR | 2455502 | 5/1979 |
| FR | 2615786 | 5/1987 |
| FR | 0269476 | 10/1987 |
| GB | 762906 | 12/1956 |
| GB | 1203305 | 8/1970 |
| GB | 2061183 | 5/1981 |
| GB | 2 277 448 A | 11/1994 |
| GB | 2324470 | 10/1998 |
| JP | 55121024 | 9/1980 |
| JP | 56139918 | 10/1981 |
| JP | 61104817 | 5/1986 |
| JP | 05245941 | 9/1993 |
| JP | 07222752 | 8/1995 |
| JP | 07300904 | 11/1995 |
| JP | 10323351 A1 | 12/1998 |
| WO | WO 88/03391 | 5/1988 |
| WO | WO 91/03211 | 3/1991 |
| WO | WO 94/18373 | 8/1994 |
| WO | WO 94/27558 | 12/1994 |
| WO | WO 96/01377 | 1/1996 |
| WO | WO 96/37163 | 11/1996 |
| WO | WO 98/42988 * | 10/1998 |
| WO | WO 01/09445 | 2/2001 |
| WO | WO 02/069817 | 3/2002 |
| WO | WO 02/38070 A1 | 5/2002 |

| | | | |
|---|---|---|---|
| WO | WO 02/087459 | 11/2002 | |

OTHER PUBLICATIONS

Reader's Digest Complete Do-it-Yourself Manual (p. 69).
The Simon and Schuster Complete Guide to Home Repair and Maintenance (p. 45).
XP-002200302, Database WPI, Section PQ, Week 198313 Derwent Publications Ltd., London, GB; Class P31, AN 1983-E3008K, SU 929 072 A (Omsk. Med. Inst und Omsk Poly).
WO/98/42988, Process for Anchoring Connecting Elements in a Material With Pores or Cavities and Connecting Elements Therefor, Publication Date: Oct. 1, 1998.
U.S. Appl. No. 10/417,645, filed Apr. 17, 2003, Mayer et al.
U.S. Appl. No. 10/661,692, filed Sep. 12, 2003, Mayer et al.
Leitgeb, N. et al.; "Die Stabilitat der Ultraschall-Osteosynthese (Stability of Ultrasound Osteosynthesis)"; Biomed. Technik, 30 (1985); pp. 44-48.
Th. Muller, Von et al.; "Grundlagenuntersuchungen zur Ultraschallchirurgie"; Z. Exper. Chirurg 15 (1982); pp. 244-250.
Forssell, H. et al.; "Experimental Osteosynthesis with Liquid Ethyl Cyanacrylate Polymerized with Ultrasound"; Traumatic Surgery (1984) 103; pp. 278-283.
Picht, U. et al.; "Sagen und Schweissen mit Ultraschall"; Z. Orthop. 115 (1977); pp. 82-89.
Kuhne, W. et al.; Heilungsvorgange an ultraschallgeschweissten Knochenfrakturen des Kaninchens (Healing processes of ultrasonically welded bone fractures in rabbits); Exp. Path. 16 (1978); pp. 102-108.
Brug, E et al.; "Die Ultraschallverschweissung von Knochen"; Chirurg 47 (1976); pp. 555-558.
Reader's Digest Complete Do-it-Yourself Manual (p. 69), 2003.
The Simon and Schuster Complete Guide to Home Repair Maintenance (p. 45), 2003.

* cited by examiner

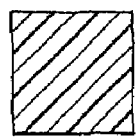  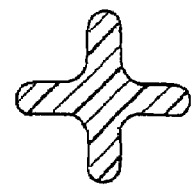 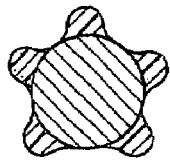
FIG.5a  FIG.5b  FIG.5c  FIG.5d
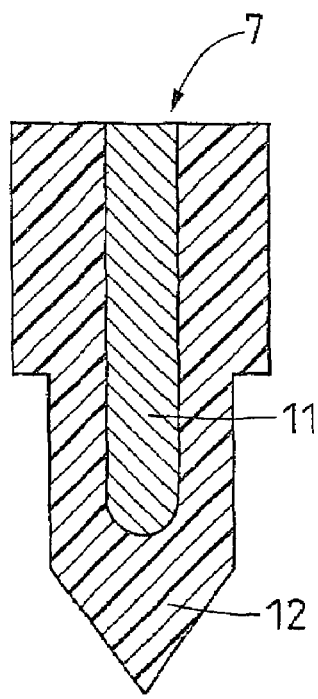 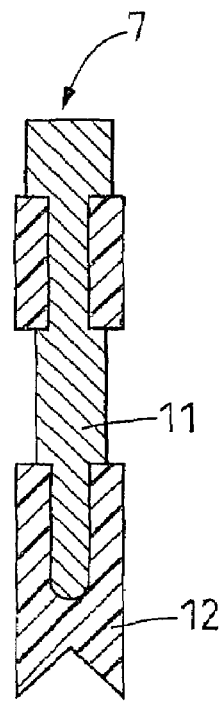 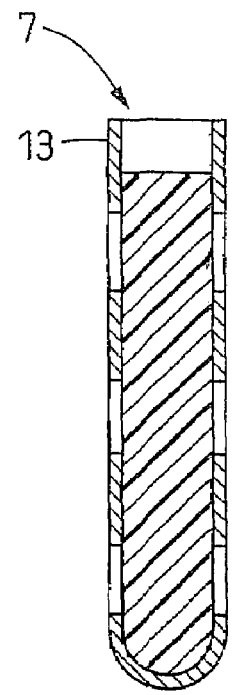
FIG.6  FIG.7  FIG.8

IMPLANTS, DEVICE AND METHOD FOR JOINING TISSUE PARTS

BACKGROUND OF THE INVENTION

The invention relates to implants for humans or animals. The implants at least partly create positive-fit connections to human or animal tissue parts, particularly skeletal parts, wherein the implants help connect tissue parts together, or help connect tissue parts to means supporting or replacing tissue parts, or to other therapeutic auxiliary devices. The invention further relates to devices and methods for implanting implants into humans or animals.

Known implants for creating connections to skeletal parts (bones) include screws, pins, agraffes etc., which are used for connecting bones to bones, or bones to artificial, carrying, stabilizing, or supporting parts, or to parts replacing skeletal parts (stabilization or fixation plates, sutures, wires, artificial joint elements, artificial teeth, etc.). Such connection elements for implantation consist for example of metal or plastic, including resorbable plastic. After healing, the connection elements are removed by a further operation or they are left in the body where they are possibly gradually decomposed and replaced by vital tissue.

For stabilizing a bone fracture, a fixation plate with suitable holes is fixed in the region of the fracture using screws as mentioned above. Plate and screws may consist of metal (e.g. stainless steel or titanium). The screws are self-cutting and are rotated into threadless openings in the bone, or they are screwed into pre-drilled threaded openings. Pins and agraffes are knocked into previously created openings for similar purposes. Connections created in the foregoing manner are usually based on frictional engagement, possibly on positive fit.

In all cases, large forces (torsional forces and impact forces) are to be applied on implantation, and possibly also on removal. This often means that the implants need to have a higher mechanical stability for implantation and removal, than for the load which they are to bear when implanted. In particular, for implants of resorbable plastic, which have a significantly lower mechanical strength than metal, this increased requirement for mechanical stability requires the implants to have relatively large cross sections, and thus, for implantation, undesirably large openings need to be created in the vital tissue.

Implantation of the named connection elements may also generate considerable quantities of heat and therewith impair the surrounding tissue, in particular due to the friction generated when producing a frictional engagement. This applies in particular to the cutting of threads, the screwing-in of self-cutting screws and the knocking-in of implants without prior drilling.

It is known also to use curable, plastic materials (e.g. particular cements on a hydraulic or polymer base) for creating connections of the mentioned type. Such materials are pressed from the outside between implant and vital tissue, or into tissue defects in a highly viscous condition, and are cured in situ. Positive-fit connections can be created using such material, if the openings into which the material is pressed comprise suitable undercuts.

It is the object of the invention to provide implants for creating positive-fit connections to tissue parts (in particular to bone parts, cartilage parts, tendon parts, ligament parts, but also to parts of other tissues), wherein the implants are able to be implanted in a simple, quick manner, with small forces, and wherein the implants are able to provide very stable connections immediately after implantation (primary stability). Furthermore, it is desired that the implants create fewer problems with regard to the generation of heat and formation of stress concentrations than is the case with at least some of the known implants, and that the volume of foreign material to be implanted is reduced. It is a further object of the invention to provide a device and a method for implanting the implants.

SUMMARY OF THE INVENTION

The objects are achieved by the implants, the device and the method of the present invention.

The invention exploits the per se known fact (e.g. from the publication WO-98/42988), that in particular, thermoplastic polymer materials can be liquefied in a targeted manner by way of mechanical oscillation and, in this condition, can be pressed into cavities (e.g. pores of wood) by way of hydrostatic pressure, thereby creating positive fit connections after solidification.

According to the invention, the implants serving for creating positive-fit connections to tissue parts consist at least partly of a material that can be liquefied at a relatively low temperature (<250° C.) by way of mechanical oscillation energy (in particular ultrasound), i.e. by internal and/or external friction, such that the material can be pressed into pores or other openings of the tissue part by the effect of external pressure to form positive-fit connections when re-solidified.

Polymers which plasticize at relatively low temperatures are suitable as the material to be liquefied by mechanical energy in the implants according to the invention, in particular thermoplasts which are already known to be medically applicable. Such thermoplasts, being non resorbable are for example: polyethylene (PE), polymethyl metacrylate (PMME), polycarbonate (PC), polyamide, polyester, polyacrylates and corresponding copolymers. Such thermoplasts being resorbable are for example polymers based on lactic acid and/or glycolic acid (PLA, PLLA, PGA, PLGA etc.), as well as polyhydroxyalkanoates (PHA), polycaprolactones (PCL), polysaccharides, polydioxanones (PD), polyanhydrides and corresponding copolymers. Per se known hydraulic or polymeric cements having thixotropic properties are likewise suitable: for example, calcium phosphate cements, calcium sulphate cements and methacrylate cements. Such cements may also contain thixotropically prepared, native tissue or transplanted materials. Due to their thixotropic properties, such cements can be brought from a highly viscous condition to a fluid condition by applying mechanical energy (in particular ultrasound) and without an increase in temperature.

For implantation, the implant according to the invention is brought into contact with the tissue part (on the surface or in an opening, which as the case may be, has been created specially for the implant), and is then impinged with ultrasound energy and at the same time is pressed against the tissue part. By a suitable design of the implant and by a suitable metering of the energy, it is ensured that only a required minimum amount of the liquefiable material is liquefied in a locally targeted manner. As soon as sufficient material is liquefied and pressed into place, the supply of energy is stopped so that the liquefied material solidifies in its new shape, with the pressure on the implant being advantageously maintained.

For implantation, the mentioned materials are thus not liquefied by external heat, but by mechanical energy (oscillation energy, vibration energy), i.e. as a result of internal and/or external friction. As a result, the thermal burden to the surrounding tissue remains low. A very high shear effect is achieved between different material phases by way of the mechanical energy. This contributes to the uniform liquefaction and achievement of low viscosity and still low burdening of the surrounding. The material liquefied in this manner is then pressed into pores or openings of the surrounding tissue by way of hydrostatic pressure, thereby permeating the surrounding tissue and enforcing it.

If so required, it may be advantageous to admix additional substances to the liquefiable material for additional functions. For example, substances may be admixed that mechanically reinforce the liquefiable material, that let the liquefiable material swell up in a secondary reaction or form pores therein, or that are to be released into the vital surroundings for promoting healing or regeneration, or that are to assume other functions. Such healing-promoting and regeneration-promoting substances may, for example be growth factors, antibiotics or inflammation-inhibitors. Such substances can be brought to a desired location or may be distributed in a tissue region in a targeted manner by the flow of the liquefied material, and in the case of a resorbable material, may be set free in a delayed manner.

Using connection implants according to the invention, pointwise or larger-surface connections can be realized. The load distribution on the connection can be influenced and controlled in a targeted manner. For example, with implants according to the invention, it is possible to fasten a fixation or stabilization plate on a bone surface either over a large surface (see e.g. FIG. 15 or 16) or pointwise and depth-effective (see FIGS. 2 to 4). More superficial connections may be achieved with plates or other support or fixation devices having integrated liquefaction zones or complete liquefaction layers, which for connection to a bone are positioned on the bone and are subsequently excited with mechanical energy (e.g. ultrasound vibration), at least locally. The liquefiable regions are advantageously provided with energy directors, or are in contact with energy directors. Energy directors that encourage local liquefaction by concentrating the oscillation energy are projecting elements, e.g. pyramids, conical, hemispherical or rib-like elements.

Depth-effective anchorages are achieved by pin-like or dowel-like implants that have a cross section (or cross-sectional geometry) that is constant or changes over their length, and that completely or partly consist of the liquefiable material. They are positioned on the surface of the tissue or in the tissue and are then excited. These implants are advantageously designed such that liquefaction starts at predefined locations (tip or specific stem regions). Controlled liquefaction may also be achieved by energy directors (projecting elements shaped in a defined manner). Depth-effective anchoring is achieved by bringing the implant into the tissue to be connected. The hydrostatic conditions can be such that the liquefied material is pressed into the adjacent tissue under a large pressure.

The device for implanting the implant according to the invention, i.e., the device for liquefying the liquefiable material in contact with the tissue part, and for pressing it into the tissue, may additionally operate to control the temperature in surrounding tissue and material, such that unreasonable quantities of heat and high temperatures and tissue damage caused thereby can be prevented. The implantation process is controlled by actively controlling the device with regard to supplied and removed energy (heat distribution and heat management) and, where appropriate, by suitably arranged sensors and heat conducting elements. Such implantation is controlled by metering the supplied energy and by dissipating excess energy.

The energy used for material liquefaction is preferably produced by piezoelectric or magneto restrictive excitation. An oscillation unit (e.g. piezoelement plus sonotrode) is actively connected to the implant (pressed against it) and is oscillated by a generator, which transmits waves in the frequency region of about 2 to 200 kHz, preferably ultrasound (e.g. 20 or 40 kHz). The implant is coupled to the bone or tissue to be connected in a manner such that the sound energy is absorbed internally or on the surface by the liquefiable material, which is thereby liquefied at least locally. The liquefaction process is achieved by a large shear effect. Internal friction and, thus, internal liquefaction can be enhanced by a second component having a different density and being locally embedded in the material to be liquefied (e.g. as globules). The same effect is exploited when using a thixotropic, particulate cement as an implant or implant part.

The connections produced by the method according to the invention are mainly positive fit connections, wherein the positive fit means may be very small on both sides (surface irregularities, surface roughness, or tissue pores) or larger (larger cavities in the tissue or between tissue parts or mechanically created openings or cavities in the tissue). The connection implants are mechanically excited by way of ultrasound in a manner such that they are liquefied in a controlled manner in particular in the contact region with the tissue part or in their interior. Liquefaction usually takes place on a tissue surface or in a suitable opening in the tissue, which opening is formed by penetrating the connection implant through the tissue surface after implantation, or by penetrating the connection implant before implantation.

The incorporation of the liquefiable material into the tissue in a depth-effective manner can in a very simplified and schematic way be compared with the effect of a piston in a hydraulic cylinder. The not yet liquefied material of the connection implant is seated in a tissue opening and essentially fills and seals it. Since the liquefied material cannot escape from the opening, a hydrostatic pressure is created on account of the load acting from the outside (pressure on the implant). Due to the pressure and the oscillation the liquefied material is pressed into existing and/or newly formed cavities of the surrounding material to be connected (vital tissue). The penetration depth depends, inter alia, on the nature of these surroundings, on the operating parameters and on the liquefiable material (in particular its viscosity). The quantity of material pressed into the tissue can be determined through the liquefiable or liquefied volume of the connection implant. If a lot of liquefied material is required, or the size and number of the cavities present in the tissue is not known, it is possible to use implants or implant components that can be supplied quasi infinitely.

Stress peaks produced by the displaced and compressed material, which may lead to failure, e.g. bursting of the tissue, are avoided by targeted application of ultrasound and mechanical or hydrostatic pressure, the two being coordinated to one another, as well as by a suitable design of the implants and the liquefiable materials arranged thereon. Cavities and gaps in the tissue are filled by the liquefied material, in the case of sufficiently porous tissue, even without pre-drilling. At the same time, the tissue in contact with the liquefiable material is compressed in a controlled manner such that the resulting retention of the connection implant is strong even in heavily porous tissue (e.g. osteoporotic bone tissue). Through the described effects, the implant according to the invention can resist large mechanical drawing forces or loads. In a later phase of the healing process, loading is reduced in a controlled manner or is taken over by regenerated tissue (secondary stabilization) if the implant is made at least partly of resorbable material.

The invention is suitable for example for anchoring a tooth prosthesis in a jaw. The tooth prosthesis preferably comprises a standardized base part designed as an implant according to the invention and being connectable to various crown parts. The base part consists completely or partly of a material being liquefiable by mechanical energy. When positioned in an opening in the jaw bone, this material is liquefied by excitation with mechanical energy and is pressed into pores of the bone tissue. As a result, the implant adapts itself to the opening and to the tissue pores, is stabilized immediately after implantation (primary stabilization) and is well-anchored, not only in the tooth root opening, but also in the adjacent bone tissue, thereby forming a suitable base part for fastening the crown part. If the liquefiable material is resorbable, the aforementioned primary stability is later, at least partly, replaced by a secondary stabilization due to regenerated bone tissue.

A further field of application of the invention is in the field of artificial joint elements. An artificial joint socket as well as a joint ball or its stem may be connected to the vital bone tissue or anchored therein by way of implants according to the invention. In addition to the gentle transmission of the loads on implantation, the materials taking part are selected such that increases in stiffness are largely avoided, which contributes positively to the life duration of the implant.

The device used for the implantation of the implant according to the invention comprises a generator for producing electrical oscillation to be transmitted to an oscillation unit via transmission means, e.g. a cable. The oscillation unit comprises an oscillation element (drive unit) and a resonator, the two being actively connected to one another. The drive unit (e.g. piezoelement) excites the resonator into oscillation. The oscillation of the resonator is transmitted to the implant directly or via a transmission means. Due to the oscillation, the implant is liquefied at least locally by inner liquefaction or by contact with a non-oscillating environment (tissue part or another implant part). During excitation, the implant may be held using a suitable holder and/or may be guided by way of a guide element. For minimally-invasive surgery, it is particularly suitable to fasten the implant directly on the oscillation unit. Holding and/or guide means may be provided, not only for temporarily holding or fixing the implant, but also for temperature management (in particular heat dissipation).

Due to the way in which the material of the implant is liquefied in a targeted and local manner, no large quantities of heat are produced. Additionally, the temperature of the tissue regions adjacent to the implant may be actively controlled by way of temperature management, for example by way of heat conducting elements, which act to dissipate heat in a targeted manner, or by way of cooling fluids (e.g. sterile ringer solution) which act in a temperature-controlling manner.

The method for implantation of the implant according to the invention on the human or animal skeleton is carried out as follows: the implant is bought into contact with the skeleton part, then mechanical oscillations are produced and transmitted to the liquefiable material of the implant whilst the implant is pressed against the skeleton part. Mechanical energy is supplied until the liquefiable material is sufficiently liquefied, and in the region of contact, penetrates into the bone tissue, or at least the surface irregularities of the skeleton part. The mechanical oscillation is then stopped for re-solidification of the liquefied material, during which it is advantageous to maintain the hydrostatic pressure. The re-solidified material anchors the implant in the skeleton part with a positive fit.

The connection implants according to the invention have the shape of pins, dowels and/or plates or films. These serve the connection of tissue parts amongst one another, or of tissue parts to artificial elements.

For implantations of the above-described manner, it is advantageous to use a kit or a set comprising at least one type of implant according to the invention, advantageously a selection of variously dimensioned implants suitable for the field of application, as well as a device for carrying out the implantation. Advantageously, the kit also comprises means for the sterile use of the device (sterile coverings for the device) and, as the case may be, exchange pieces of components (in particular resonator, distal resonator part or transmission part) being able to be sterilized. By way of different shapes, the resonator parts are adapted to various implants and/or applications. Furthermore, the kit advantageously comprises instructions for implantation, details on implantation parameters and further auxiliary means for preparing the tissue part (e.g. drills matched to the implants), positioning instruments, control instruments and/or implant guides adapted to implants and/or resonators.

The kit or set is preferably kept complete by subsequent provision of implants. The selection is made according to the demands and may change with time. The subsequent provision of implants (replacement and addition kit) comprises replacements for used implants, as well as the provision of new implant types and again includes suitable means for tissue preparation, positioning instruments, control instruments, adapted resonators or resonator parts, implant guides and, in particular, corresponding implantation instructions.

BRIEF DESCRIPTION OF THE DRAWINGS

The invention is explained in more detail by way of the subsequent Figures, wherein:

FIGS. 5a to 5d show exemplary cross sections of pin-like implants according to the invention, wherein the implants comprise axially extending energy directors;

FIGS. 6 to 8 show longitudinal sections through two exemplary, pin-like implants according to the invention, wherein the implants comprise implant parts of a non-liquifiable material;

DETAILED DESCRIPTION OF THE PREFERRED EMBODIMENTS

Figure 1:
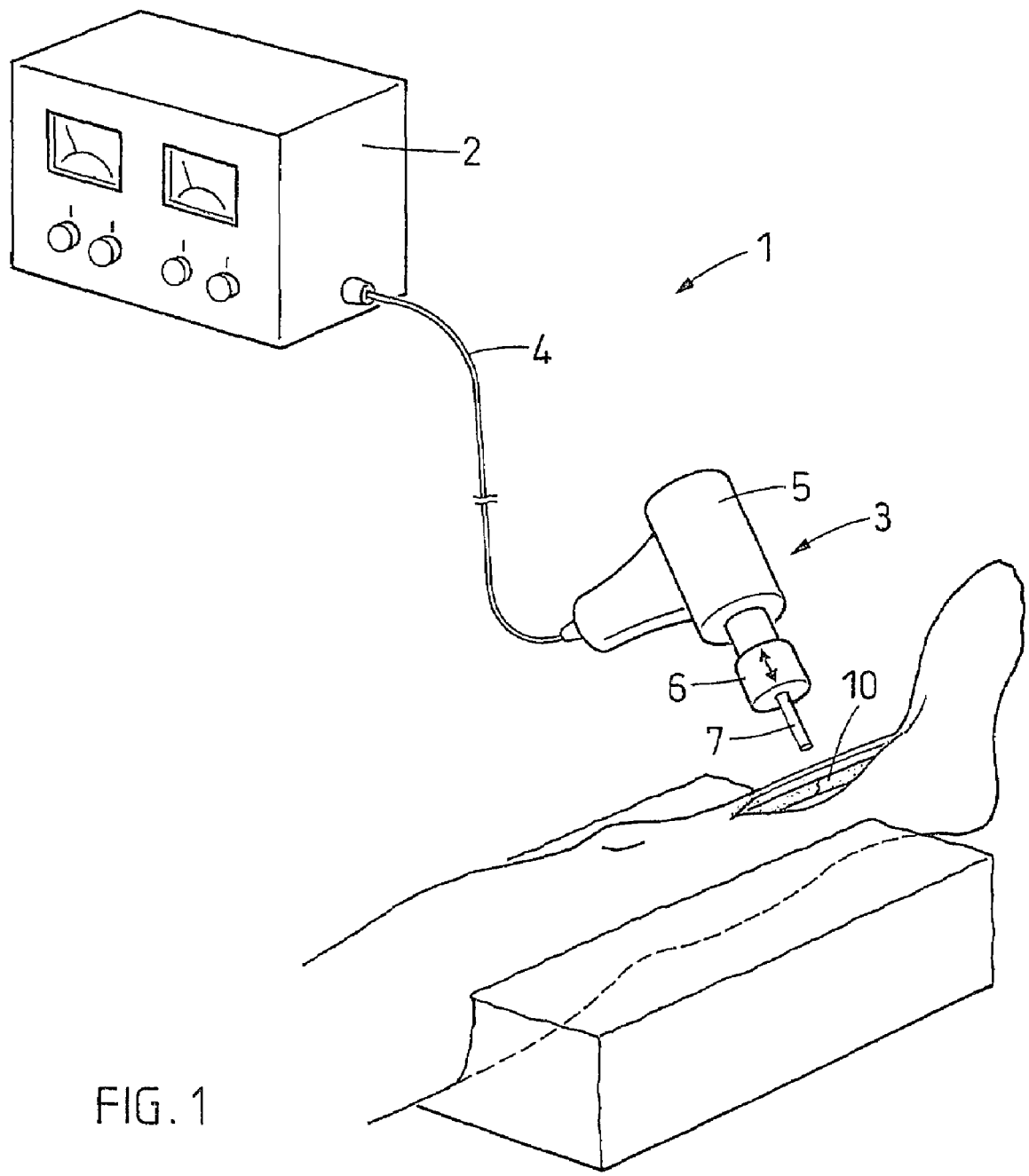
FIG. 1 shows an exemplary embodiment of the device for implanting implants according to the invention, and its use.

Schematically, and in a very simplified manner, FIG. 1 shows an exemplary embodiment of an implantation device 1 applicable for implanting implants according to the invention.

The device 1 comprises a generator 2 and an oscillation unit 3 connected together via a cable 4. The oscillation unit 3, which is partly accommodated in a housing 5, is designed as a hand apparatus to be used like a hand drill, for example. The oscillation unit 3 comprises an oscillation element integrated in the housing 5 (not shown in detail) and actively connected to a resonator (sonotrode) 6. At least a distal resonator part projects out of the housing 5. The generator 2 supplies the oscillation element with energy. Excited by the oscillation element, the resonator oscillates at a predefined frequency or, as the case may be, with a predefined frequency pattern. Frequencies of 2 to 200 Hz and resonator amplitudes of 1 to 100 µm in the direction (z-direction) indicated by the double arrow are particularly suitable. The frequencies may be set depending on the application, the materials to be liquefied and the shape of resonator and implant. It is also conceivable to superimpose additional mechanical oscillations, such as with a lower frequency and larger amplitude on the vibrations in the ultrasound region. In many cases, it is sufficient to design the device for a single oscillation frequency, for example for 20 or 40 kHz and for a resonator amplitude of approximately 20 or 30 µm in the z-direction (direction in which an implant 7 is pressed by the resonator 6 against a tissue part). In order to control the power (supplied energy per unit of time), the excitation may be pulsed, wherein pulse distances and/or pulse lengths are set.

Advantageously, and in a per se known manner, the oscillation frequency and the resonator shape are matched to one another such that the resonator oscillates in a standing wave and such that its distal end, which is pressed against the implant, has a maximum amplitude in the z-direction. It is further advantageous to give pin-like implants a length that is matched to a predefined excitation frequency and predefined implant material.

The distal end of the resonator 6 may be designed for holding an implant 7, as is shown in FIG. 1. This simplifies positioning of the implant on a tissue part or in an opening of a tissue part, such as the bone of a leg 10. For positioning and implantation without an opening, it may also be advantageous to provide an implant guide that is supported on the housing 5 or on the tissue part. It is also possible to design the resonator with a planar end face like a hammer and to simply press it against an implant held in a tissue opening or held by way of a suitable separate mounting or guide means. The distal end face of such a resonator must not stick to the implant during implantation. This is achieved by a suitable, non-adhering end-face of the resonator or by an implant part adjoining the resonator part that consists of a non liquefiable material.

For applications in a sterile operation region, the device may be used in a sterile covering. Advantageously, the sterile covering comprises an opening for the distal part of the resonator, and the resonator or a distal resonator part can be removed for exchange and sterilization.

Other exemplary embodiments of the implantation device 1 according to the invention can be designed as hand-held apparatus comprising all components (including energy supply) or as completely stationary apparatus.

Figure 2:
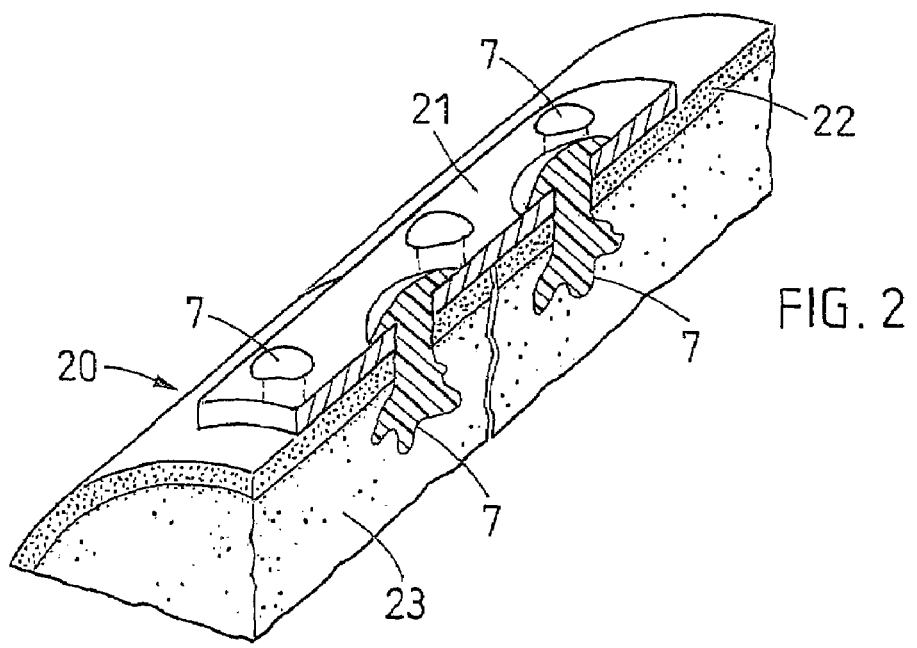
FIG. 2 shows a fixation plate fastened on a bone by implants according to the invention.

FIG. 2 shows a fixation or stabilization plate 21 being fastened by implants 7 according to the invention on a bone part in the region of a bone fracture or laceration, in order to stabilize the fracture or laceration. The bone part 20 in this case comprises a relatively thin, but relatively compact, outer cortical layer 22 disposed above cancellous bone tissue 23 which is porous. Other than shown in FIG. 2, the transition of the cortical bone to the cancellous bone in natural tissue is a gradual transition in which the tissue becomes more and more porous. The implants 7 extend through openings in the plate 2, through the cortical bone substance 22 and into the cancellous bone 23 and they are anchored at least in the cancellous bone 23.

Figure 3:
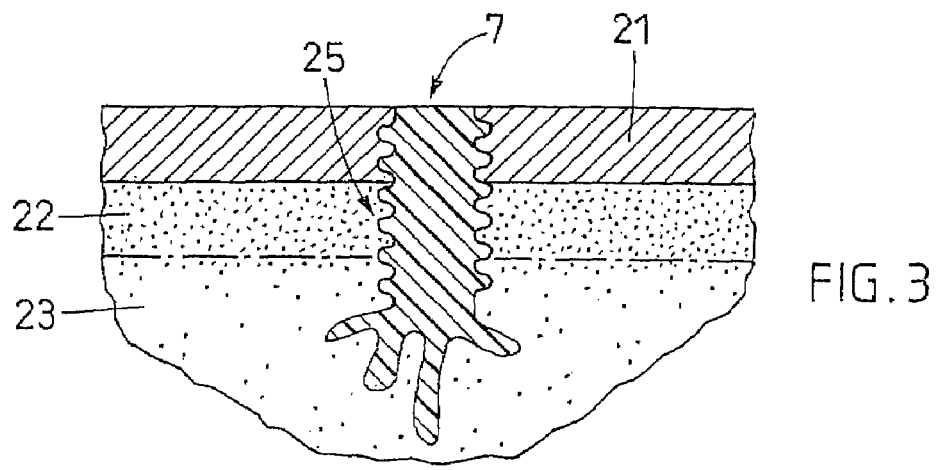
FIGS. 3 and 4 show examples of implants according to the invention, to be used e.g. in the application according to FIG. 2, and connections between bone and plate created therewith.
Figure 4:
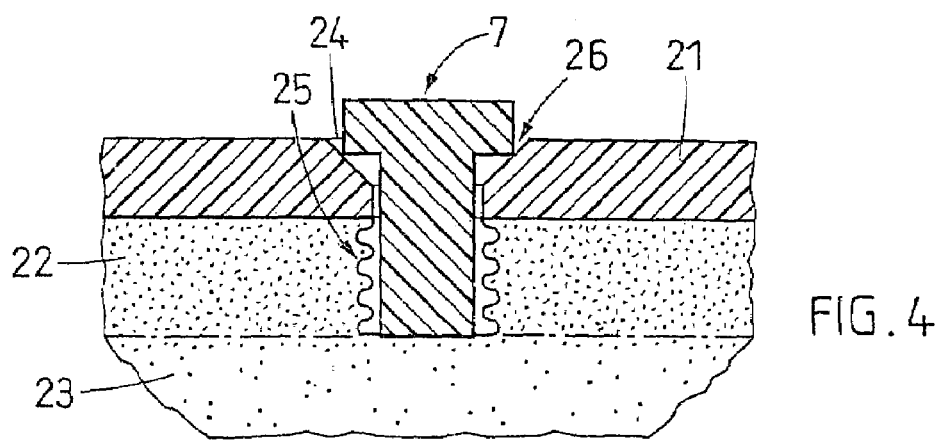

FIGS. 3 and 4 in section and in an enlarged scale, show two examples of implants according to the invention that may be used for the application shown in FIG. 2. FIG. 3 shows an implant after implantation. FIG. 4 shows another implant that is positioned in an opening 24 of plate 21 and cortical bone substance 22 and is ready for impingement with oscillation energy.

For implantation, at least the cortical substance layer is to be opened, for example by drilling. A suitable bore may also continue into the cancellous bone 23 as a pocket hole. Since the cortical substance of the bone has no suitable pores for pressing in the liquefied material, such openings or surface irregularities may be created by cutting a thread 25 or by roughening the inner walls of the bore. The liquefied material is then pressed into such openings and re-solidified to form a positive-fit connection. The liquefied material of the implant is pressed into the pores of the cancellous bone 23, and, in this manner, the implant 7 is anchored in a depth-effective manner. It shows that hydrostatically pressing a liquid material into the tissue pores is significantly gentler on the tissue than mechanically introducing a solid material. For this reason, it is possible to create stable connections to tissue not having much mechanical strength, e.g., to osteoporotic bone tissue.

In order to connect the implant 7 to the plate 21, the implant may have a head that is like a mechanical screw, such as is shown in FIG. 2. As shown in FIG. 3, the opening in the metallic plate 21 may also comprise an inner thread that is like the thread created in the cortical substance 22 of the bone. The liquefied material penetrates and solidifies in these threads, thereby forming a positive fit. In this case, an implant head is not needed. The implant 7 is aligned flush to the plate 21 by driving a suitably dimensioned implant to the desired position, thereby avoiding undesirable trimming of a projecting implant part.

For a plate 2 consisting of a thermoplastic plastic, the connection between plate and implant (securement against loosening) may be accomplished as shown in FIG. 4, wherein a material-fit connection (welding or adhering) is formed at the same time the implant is anchored in the tissue. On driving in the implant, this material-fit connection begins to form at the connection location 26. In this case as well, the implant 7 is advantageously driven so far in that, in the end, it is flush with the outer side of the plate 21.

Since the implant 7 does not need to be rotated into the tissue, it does not need to include means for coupling in a relatively large torsional force, as is as required for known screws. Dimensioning of the implants can therefore be determined purely by their function in the implanted condition. As such, the implants are more streamline and the openings that need to be created in the tissue are smaller than is the case with conventional screws of the same material. Since the positive-fit is formed by liquefaction and resolidification of the material, it comprises less stress and notches, which further increases its strength and makes it less prone to material fatigue.

Implants according to the invention to be anchored in the tissue part in a depth-effective manner, as shown in FIGS. 2 to 4, are advantageously pin-like or dowel-like and comprise the liquefiable material for example at their distal end, as well as on further surface regions at which an anchoring is desirable (e.g. in a thread in plate 21 and cortical substance 2 of the bone). In fact, as shown in FIGS. 2 to 4, the implants may completely consist of the liquefiable material, wherein the distal end and the surface regions at which the material is to be liquefied in particular are advantageously provided with energy directors, or energy directors are provided at surfaces coming into contact with these regions. Such energy directors may be distal implant ends that are pointed or taper to one or more essentially point-like or linear tip regions. Further surface regions to be liquefied may include humps, tips or ribs whose height and widths are to be adapted to the anchoring being created. The energy directors project at least 10 μm beyond the surface. They may also be significantly larger and may be designed as axially-running ribs rendering the pin cross section humped or cornered, as is shown in an exemplary way by FIGS. 5*a* to 5*e*. Pin-like implants have such cross sections over their entire length, or only over a part of their length.

For pin-like implants to be anchored in the region of their cylindrical surface only, or in addition to anchoring in the region of the distal end, tissue openings (e.g. bores) are provided such that introduction of the implant causes (at least locally) a friction fit between tissue and implant or energy directors respectively, i.e. the tissue openings are slightly narrower than the cross section of the implants.

For further functions, the liquefiable material may contain foreign phases or further substances. In particular, the material is mechanically strengthened by admixture of fibers or whiskers (e.g. calcium phosphate ceramics or glasses). The liquefiable material may further comprise in situ swelling or dissolvable, i.e. pore-forming constituents (e.g. polyester, polysaccharides, hydrogels, sodium phosphate) and substances to be released in situ, e.g. growth factors, antibiotics, inflammation reducers or buffers (e.g. sodium phosphate) to combat the negative effects of an acidic breakdown. Admixtures for furthering visibility in x-ray pictures and similar functions are conceivable also.

It has been shown that when anchoring implants in cancellous bone (wherein the implants have a construction according to FIGS. 2 to 4, are composed of polymers such as PC or PLLA and have a diameter of 3 to 4 mm) forces in the region of 0.5 to 5 N per $mm^2$ implant cross section are advantageously used for the pressing-in. Forces in the named range result in a driving-in speed greater than 5 mm/s.

FIGS. 6 to 8 show three further, exemplary pin-like implants 7, which, in addition to regions of liquefiable material, comprise a core 11 (FIGS. 6 and 7) or a sleeve 13 (FIG. 8) composed of a non-liquefiable material, such as metal, ceramic or glass, or a composite material.

The implants according to FIGS. 6 and 7 comprise at their distal end a cap 12 of the liquefiable material, which is more or less pointed (FIG. 6) or comprises a plurality of pointed or linear end regions (FIG. 7). The cylindrical surface of the core 11 is completely surrounded by liquefiable material (FIG. 6) or only in regions, wherein these regions extend axially, or annular (FIG. 7) or may be regularly or irregularly distributed over the core surface. These regions advantageously comprise energy directors as described above for implants consisting entirely of liquefiable material. The liquefiable material is to be thicker or thinner, depending on the desired penetration depth, but should not be thinner than approx. 10 μm.

Step-like reductions in cross section as shown in FIG. 6 are suitable as energy directors. Implants with such steps are advantageously implanted in correspondingly stepped or narrowing tissue openings.

The impingement of a pin-like or dowel-like implant with a non-liquefiable core 11 may either concern the complete proximal end of the implant or only the annular outer region consisting of the liquefiable material.

The implant according to FIG. 8 comprises the liquefiable material in the inside of a non-liquefiable sleeve 13. The sleeve 13 is provided with openings arranged in places where anchoring is desired. Such an embodiment of the implant according to the invention is suitable in particular for the application of highly viscous, thixotropic materials as liquefiable material since such a material cannot withstand the mechanical loading caused by the resonator pressing on the implant. The openings in the sleeve are to be dimensioned in a manner such that the highly viscous material can only get through when liquefied. Sleeves 13 of porous sintered material are particularly suitable. An implant with a sleeve 13 is to be positioned in a tissue opening and the resonator is applied only on the liquefiable material, i.e. has a cross section adapted to the inner cross section of the sleeve.

At the proximal end of a pin-like or dowel-like implant there may be provided a head-like thickening, an artificial part replacing or fixing a further tissue part, a therapeutic auxiliary device, fastening means for such a device, or a fixation means for a suture or cerclage wire. The proximal end may also be equipped as a holding means cooperating with a corresponding holding means on the resonator (see FIGS. 9 to 11).

A metallic core 11, for example in a pin-like or dowel-like implant, usually serves as a mechanical reinforcement of the implant and is suitably dimensioned for this application. The core may, however, also be significantly thinner and easily removable from the implant. In this case, it provides visibility in an x-ray picture during minimally-invasive implantation, and may serve as a guide wire. The core is removed directly after implantation.

An implant comprising a metallic core and being anchored in the tissue according to the invention and comprising a liquefiable material that is resorbable has a good primary stability immediately after implantation. On resorption of the anchoring material, the anchoring loosens or is made dynamic, such that more and more load has to be carried by the tissue itself. This encourages the regeneration process and prevents the atrophy process in many cases. After decomposition of the liquefiable material, the core can be removed easily if its surface is designed such that the vital tissue does not grow together with it. If its surface, however, is designed in a manner such that tissue intergrowth is promoted (bioactive surface), this intergrowth constitutes an ideal, secondary stability for an implant or implant core remaining in the tissue (see also FIG. 28).

Implant cores as shown in FIGS. 6 and 7 may not only consist of metal (e.g. steels, titanium or cobalt-chrome alloys), but according to their application, may also consist of polymers (e.g. polyetheraryl ketone, polyfluoro—and/or polychloroethylene, polyetherimides, polyethersulphones, polyvinylchlorides, polyurethanes, polysulphones, polyester) or of ceramic or glass-like materials (e.g. aluminium oxide, zirconium oxide, silicates, calcium phosphate ceramics or glass) or of composite materials (e.g. carbon fibre reinforced high-temperature thermoplasts).

Figure 9:
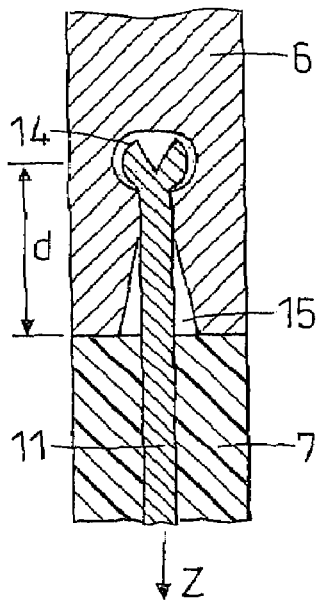
FIGS. 9 to 13 show exemplary embodiments of cooperating holding means on pin-like or dowel-like implants and resonators.
Figure 10:
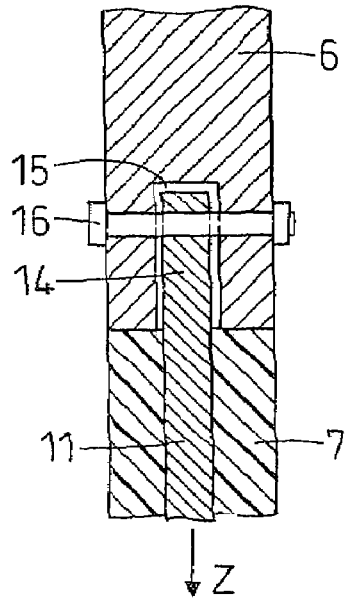

FIGS. 9 to 13 show various exemplary applications for holding a pin-like or dowel-like implant according to the invention in or at the distal part of the resonator 6 (sonotrode) of the implantation device 1 (FIG. 1). The holder may for example be a positive-fit holder as shown in FIGS. 9 and 10. The positive-fit for example is realized as a snap-closure (FIG. 9) of a resiliently designed proximal extension 14 of an implant core 11 or implant 7 which is introduced into a corresponding opening 15 at the distal end of the resonator 6. The positive-fit may also be realized by a suitably secured pin 16 extending through the resonator 6 and the proximal extension 14 of an implant core 11 or implant. Advantageously, the positive-fit is arranged at a distance d to the distal end of the resonator such that it lies in a node point of the oscillations in z-direction, i.e. in a position in which the amplitude in z-direction is essentially zero.

Figure 11:
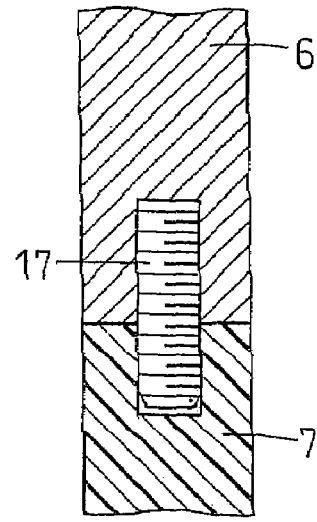

FIG. 11 shows a screwed connection 17 between resonator 6 and implant 7, i.e. a non-positive fit or force-fit connection. If this connection is biased in a manner such that the oscillations propagate uninterrupted from the resonator to the implant, the implant 7 becomes a part of the resonator 6 and is to be designed accordingly. This means that the distal end of the resonator does not necessarily require maximal amplitude in the z-direction, but may as well lie on a node point.

Figure 12:
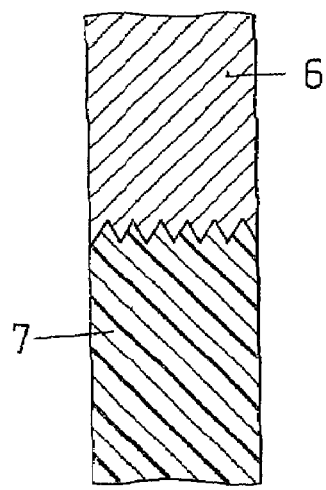
Figure 13:
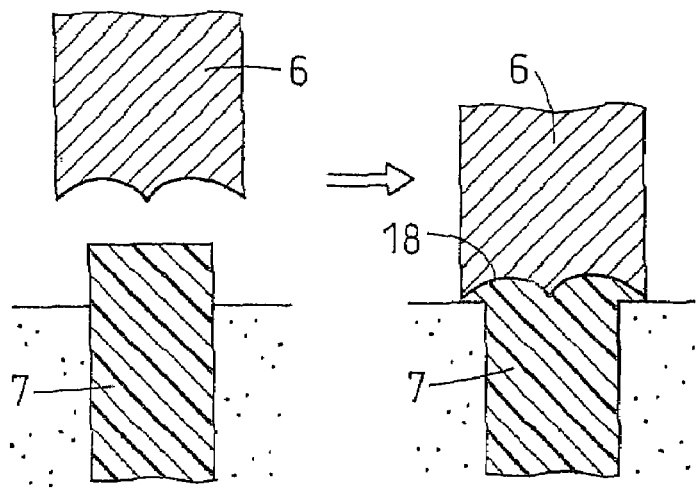

FIGS. 12 and 13 show advantageous implant holders on the resonator 6 for implants whose proximal end consists of the liquefiable material. In both cases, the proximal implant end is shaped by and bonded to the distal end of the resonator 6 due to the ultrasound effect and suitable energy directors arranged on the resonator. FIG. 12 shows a resonator 6 with a distal surface which is formed as the impact surface of a granulating hammer. FIG. 13 shows a resonator 6 with a central energy director. In both cases, the proximal end of the implant 7 is contacted by the energy directors of the resonator 6 and the resonator is set into oscillation. The liquefiable material in the region of the energy directors of the resonator is liquefied first and bonds to the resonator, wherein it assumes the shape of its distal surface and forms a head 18 in the case which is shown in FIG. 12.

Holding of the implant on the resonator as shown in FIGS. 9 to 13 is advantageously established before positioning the implant on or in the tissue part, and it is released after implantation, in the cases of FIGS. 12 and 13, by way of a force with which the resonator is bent away or rotated off the implant 7.

Figure 14:
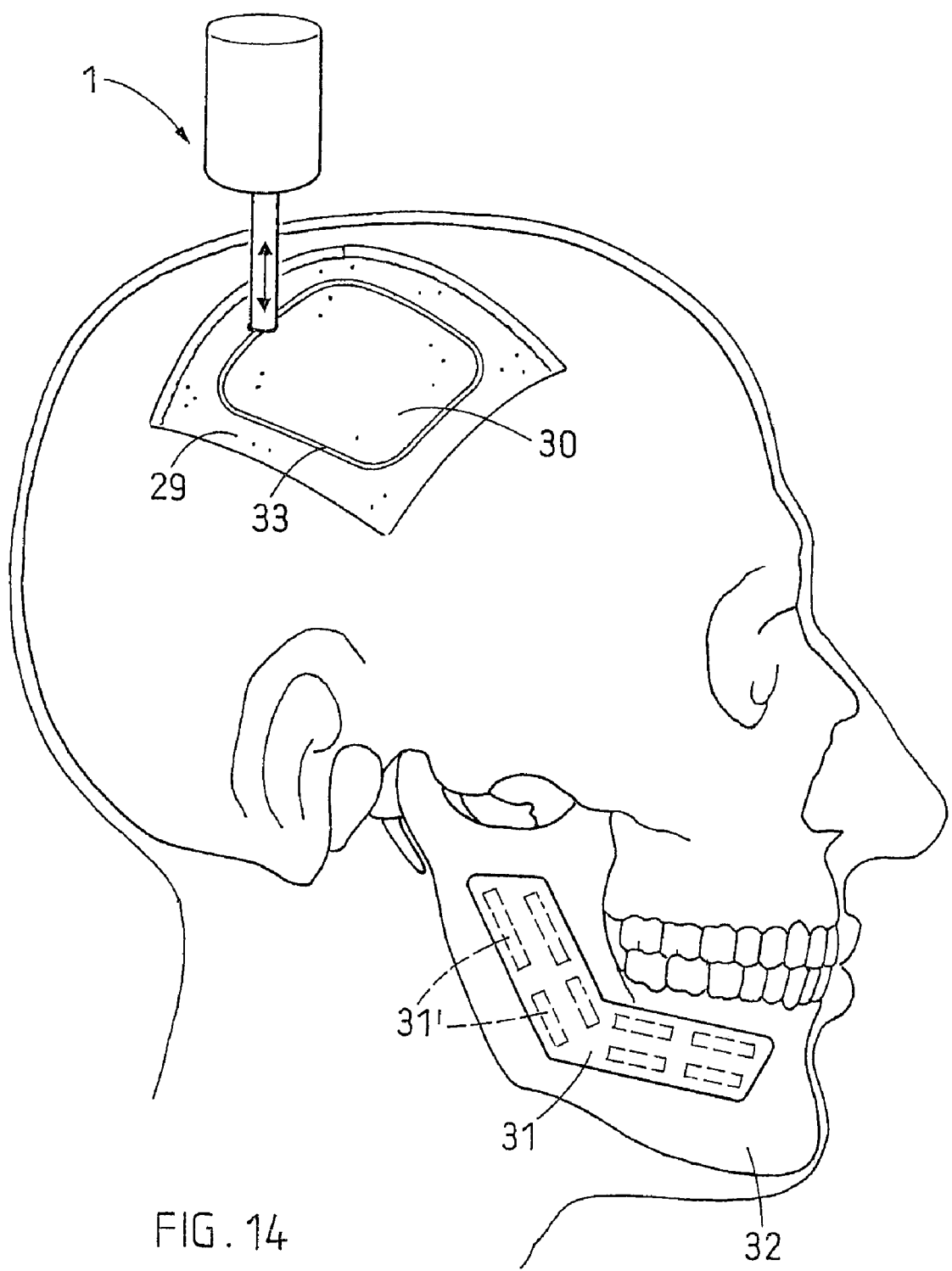
FIG. 14 shows applications of implants according to the invention on a human scull or jawbone.

As an example of further fields of application for implants according to the invention, FIG. 14 shows the fixation of a cover plate 30 of bone or of a man-made material into an opening of the calvaria 29 and the fixation for example of an artificial fixation plate 31 on a broken or fractured jawbone 32. Similar applications are conceivable in reconstruction surgery in the facial region. The connections that are to be created between the cover plate 30 and the surrounding bone tissue are advantageously limited to selected locations of the gap 33 between the plate and the native bone. The fixation plate 31 is likewise connected to the jawbone at selected plate locations 31'. The connections at the selected locations are realized in successive implantation steps using the implantation device 1.

Figure 15:
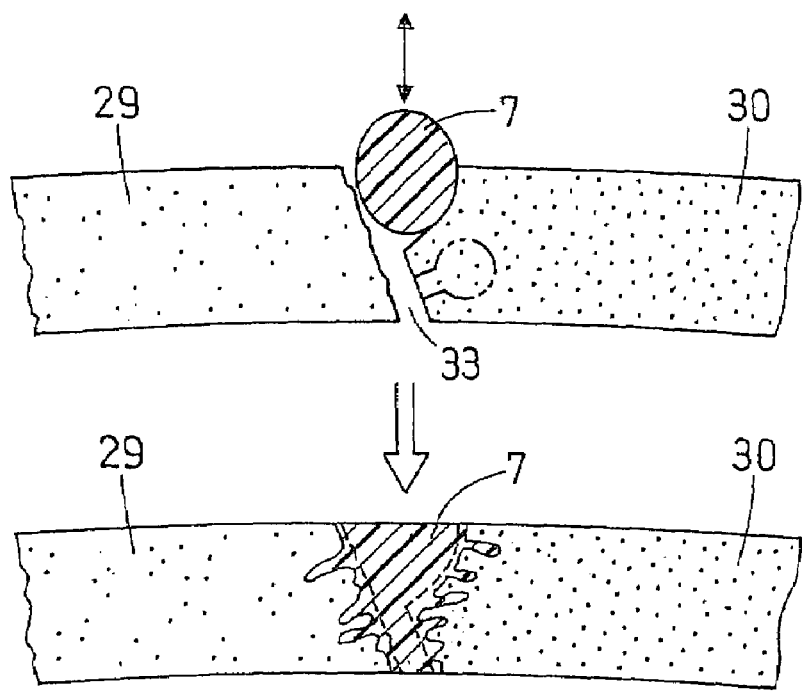
FIGS. 15 to 17 show implants applicable e.g. in the scull region and exemplary connections between two scull parts created therewith.
Figure 16:
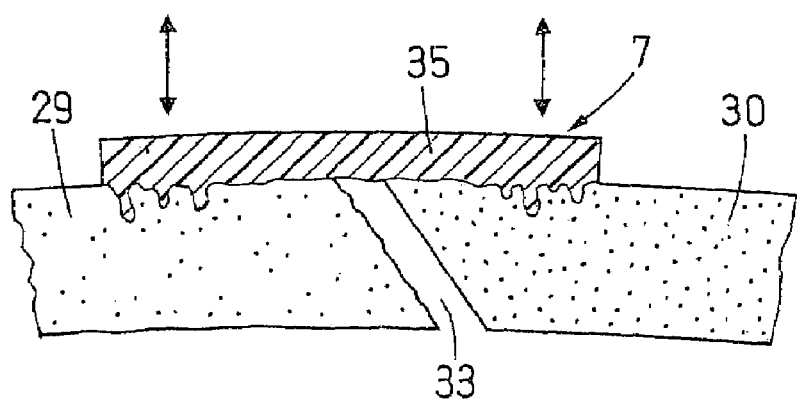
Figure 17:
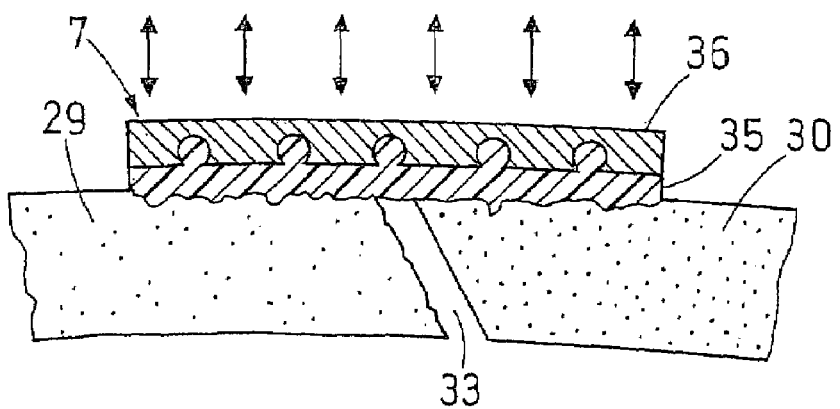

In section and in an enlarged scale, FIGS. 15 to 17 show connections that may be created with implants 7 according to the invention and that, for example, are suitable for the applications shown in FIG. 14.

FIG. 15 shows an implant 7 according to the invention that may be used to provide at least a local connection between the scull 29 and the cover plate 30, which is to be fixed in an opening of the scull that may contain porous material (e.g. likewise scull bone). The implant 7 is positioned (above) and then implanted by way of ultrasound energy (double arrow) in order to connect the scull 29 and the cover plate 30 across the gap 33 (below).

The gap 33 is advantageously formed obliquely in a manner such that external pressure forces on the gap region are accommodated by the calvaria 29. On the outer side, the gap 33 is extended for positioning the implant 7. The implant, which for example, is spherical or sausage-like and consists of a thermoplastic or thixotropic material, is positioned in the extended outer gap region and is impinged with oscillation energy. As a result, the implant material is liquefied, and on the one side, is pressed into the pores of the calvaria 29, and on the other side, is pressed into corresponding pores of a cover plate 30 consisting of, for example, bone, or into correspondingly arranged artificially created openings (e.g. dot-dashed groove) in an artificial plate. A positive-fit anchoring is thereby created on both sides such connecting calvaria 29 and cover plate 30.

FIG. 16 shows a fixation foil 35 which may also have the form of a textile web and which may, for example, be applied for local fixation of the cover plate 30 in the opening of the scull 29. The foil 35 is, for example, tape-like and is advantageously flexible. It consists completely of a liquefiable thermoplast or is, for example, reinforced with a fiber mat, or with a similar structure. It is applied over the gap 33 and is excited on both sides (double arrows) with the help of an implantation device (FIG. 1) in a manner such that it adheres to the surface of the calvaria 29 and the surface of the cover plate 30 (larger-surfaced, less depth-effective connection which may be limited to a multitude or a pattern of individual fixation points). As the case may be, the surface regions, at which the implant is to be connected to the material lying therebelow, may be suitably pre-treated (e.g. roughened) or suitable surface structures (surface unevennesses, recesses, grooves etc.) are provided on the artificial plate 30. In order to conncet the film 35 to a bone surface, a pressure on the order of 0.5 to 3 N per mm$^2$ of resonator end face is sufficient.

FIG. 17 shows a fixation plate 36 that is fastened with the help of a fixation film 35 or corresponding textile web over the gap 33 and which, for accommodating accordingly larger forces, consists e.g. of metal. Therefore, in addition to being used in a skull application, the fixation plate 36 may also be used on the jaw as shown in FIG. 13 or in the application according to FIG. 2. The fixation plate 36 consists of a material that is not liquefiable in the context of the invention. On a surface directed towards the tissue to be fixed, the fixation plate 36 has a surface structure suitable for a positive fit. The film 35 is positioned between the plate 36 and the tissue or material to be fixed and through the plate 36 is impinged at least locally with oscillation energy and is thus connected to the surface of the calvaria 29 and to the cover plate 30. The positive-fit connection between film 35 and fixation plate 36 may be created during implantation, or the plate 36 with the film 35 already connected to it may be used as a finished implant. In such a two-layer implant the connection between the layers may also be of a material fit (adhesion or welding). The film 35 in such a two-layer implant may also be reduced to a coating of the plate, wherein the coating advantageously does not have a constant thickness, but has energy directors consisting of a pattern of humps, points or ribs that have a minimal height (coating thickness) of approx. 10 μm.

The fixation plate 31 shown in FIG. 14 comprises film regions 31' arranged for example in suitable recesses and having an outer surface provided with energy directors. These film regions are connected to the jawbone regions lying thereunder.

Figure 18:
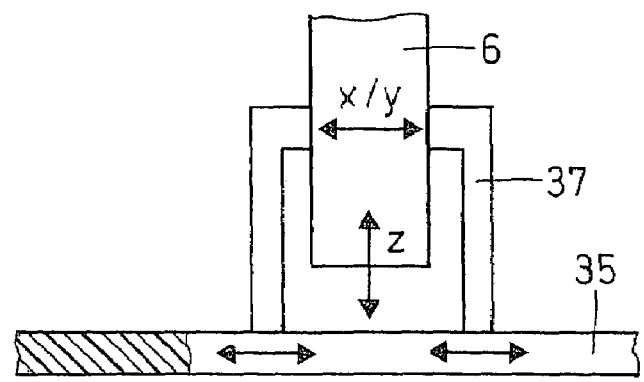
FIG. 18 shows an exemplary resonator arrangement for applications as shown in FIGS. 16 and 17.

It may be advantageous for the application shown in FIG. 16 to design the resonator to be used in a manner such that the oscillations transmitted to the implant are not aligned perpendicular (z-direction) to the connection plane to be created as indicated with double arrows, but parallel to this (x/y-direction). As the case may be, a transmission element 37 as shown in FIG. 18 is suitable. This transmission element 37 is connected to the resonator 6 with a non-positive fit and specifically at a location in which the wave in the z-direction has a node point (amplitude=0) and thus the wave in the x/y direction has a maximum amplitude. This oscillation in the x/y direction is transmitted to the film 35 by the transmission element 37.

Figure 19:
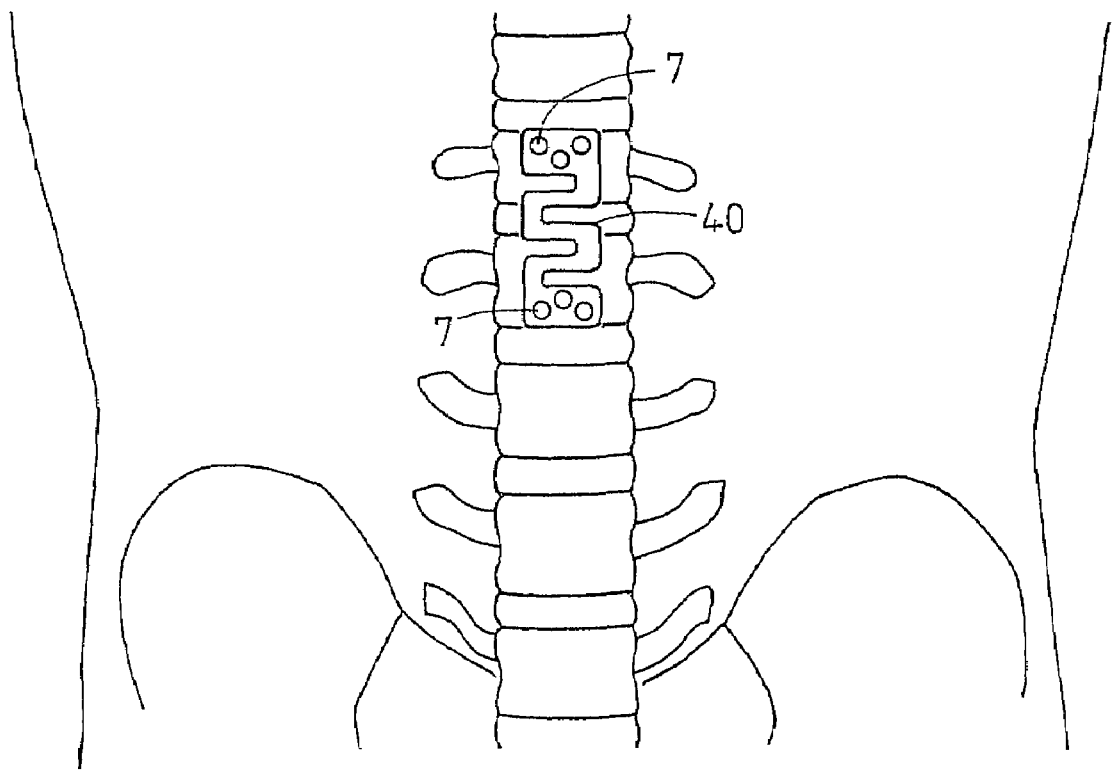
FIG. 19 shows a further application of implants according to the invention in the region of the human vertebral column.

Schematically and in a greatly simplified manner, FIG. 19 shows a further application of implants according to the invention, namely a support element for a human vertebral column region. The support element 40 is elastic and supports the vertebral column region in a lasting or possibly temporary manner. In the context of the invention, the support element 40 is fastened to vertebral bodies in that it consists of a correspondingly liquefiable material and is fastened without depth effectiveness (as shown in FIG. 16), in that it consists of a non-liquefiable material and is connected to the vertebral bodies through a film and without depth effectiveness (as shown in FIG. 17) or with predrilling and depth effectiveness (as shown in FIGS. 2 to 4). The pin-like implants 7 shown in FIG. 19 have, for example, a head projecting beyond the support element and are made according to FIG. 13. For a lasting support, connecting implants and support element are made of a non-resorbable material. For a temporary support, connecting implants and support elements are made of a resorbable material.

Figure 20:
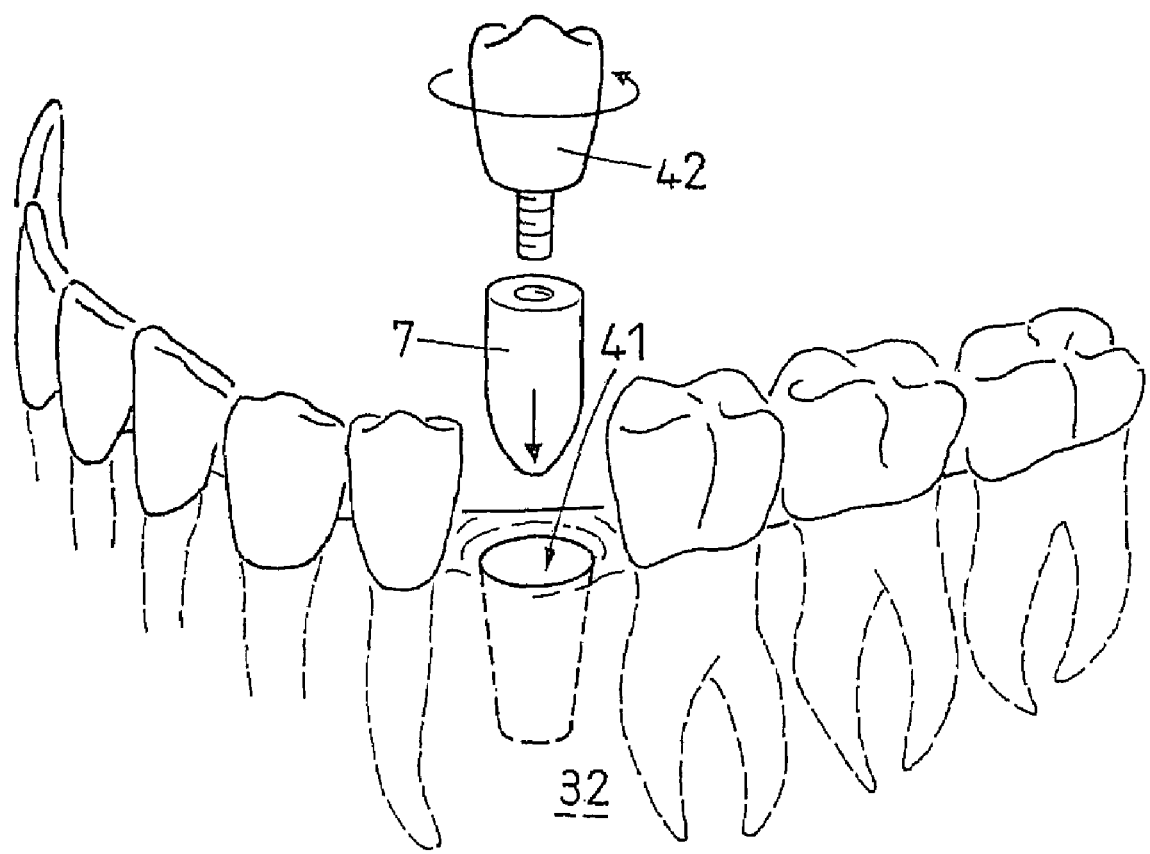
FIG. 20 shows a further application of implants according to the invention for fixing a tooth replacement.
Figure 21:
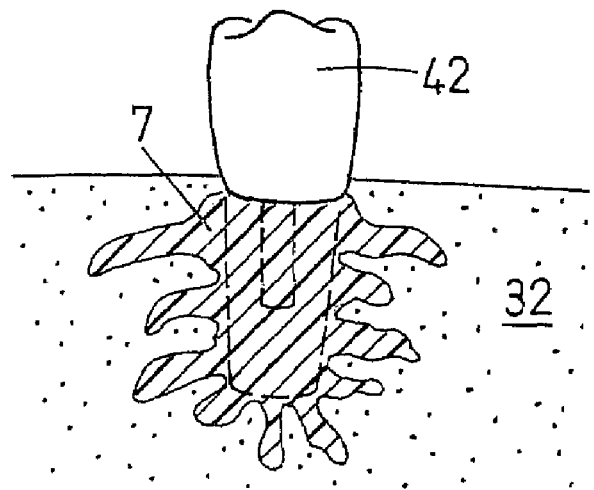
FIGS. 21 and 22 show in section two exemplary implants according to the invention suitable for the application as shown in FIG. 20.

FIG. 20 shows the application of a dowel-like implant 7 according to the invention forming a basis for an artificial tooth 40 in a jawbone 32. The implant 7 consists, at least partly, of a thermoplastic or thixotropic material. On its end face, it comprises means for holding the artificial tooth 40, a bridge or prosthesis. The implant is positioned in the corresponding opening with or without the artificial tooth and is pressed in further under ultrasound vibration. Since at the same time at least a part of the implant liquefies, it not only fills gaps between implant and bone in a largely interstice-free manner, but is also pressed into the pores of the jawbone so that a depth-effective connection arises as is for example shown in section in FIG. 21.

Figure 22:
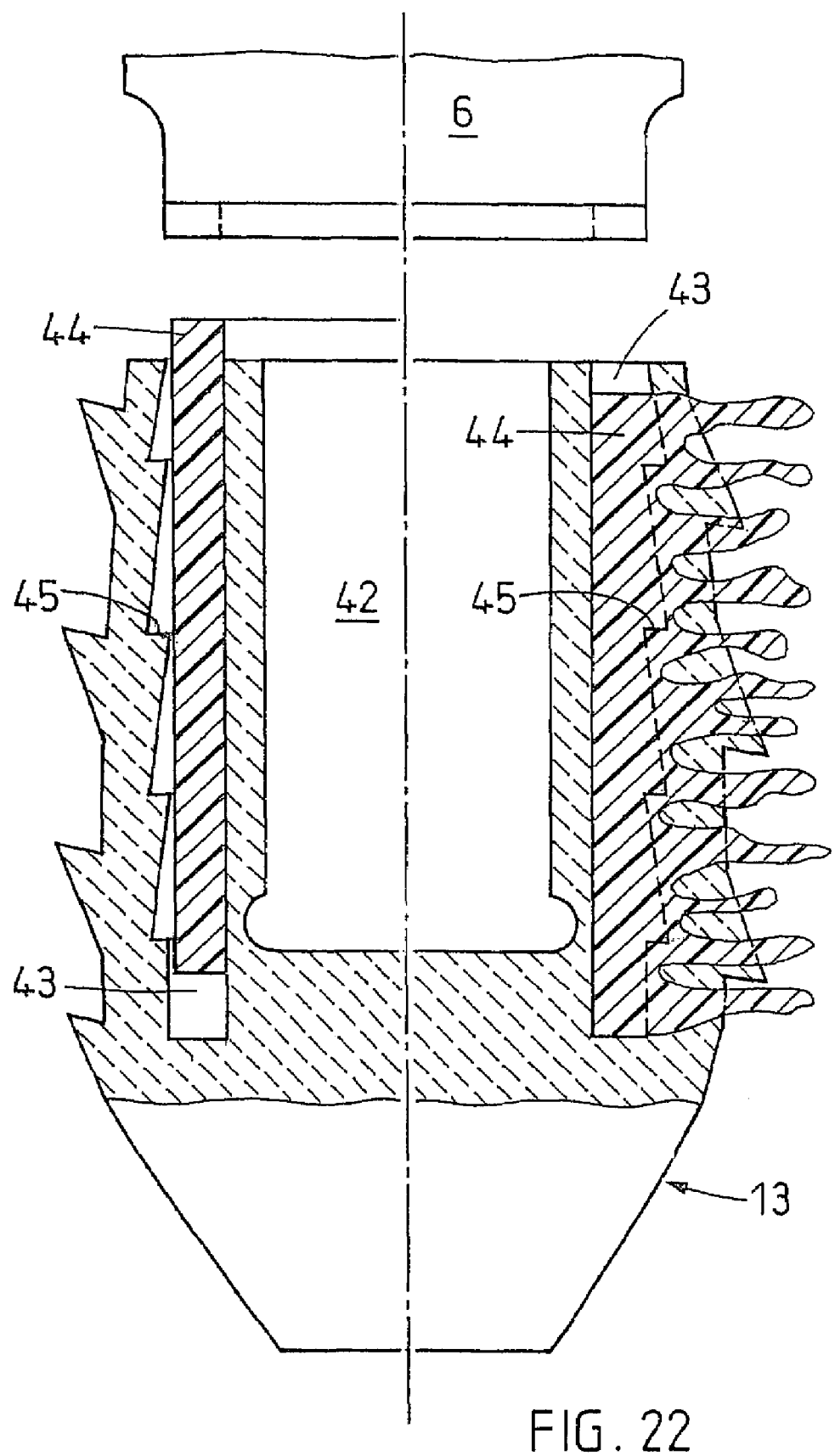

FIG. 22 shows in section a further exemplary embodiment of an implant according to the invention. This implant is particularly suitable for the application shown in FIG. 20. The liquefiable material is not arranged on the outer surface of the implant, but within a sleeve 13 which is permeable to the liquefiable material when liquefied, as has already been described in connection with FIG. 8. The longitudinally sectioned implant is shown to the left of the middle line in a state before application of ultrasound and to the right of the middle line in a state after the application of ultrasound. The sleeve 13 consists, for example, of a metallic or ceramic sintered material with an open porosity, and assumes the bearing function of the implant. In the shown case, it comprises an opening with an inner thread suitable for fastening a tooth, bridge or tooth prosthesis. The implant comprises a further, annular opening 43 in which the liquefiable material is positioned, for example a cylindrical piece 44 of the liquefiable material. For a targeted liquefaction, energy directors 45 are provided in the inside of the annular opening 43 in contact with the liquefiable material.

The implant according to FIG. 22 is, for example, positioned in an opening of a jawbone (41, FIG. 20) and then the liquefiable material is impinged with mechanical energy using a resonator 6 with an annular distal end. As a result, this material is liquefied and pressed through the porous sleeve material, into the surrounding bone tissue, whereby the implant is anchored in this tissue.

For the application shown in FIGS. 19 to 20, it is particularly advantageous to select a resorbable material as the liquefiable material, whilst the bearing part consists of a material that is neither liquefiable nor resorbable and that has a sufficient mechanical strength for the fastening of a tooth, bridge or prosthesis. At the same time, at least the surface of the central part is bioactive (e.g. porous as described for the sleeve 13), that is to say, equipped in a manner such that it promotes an intergrowth with bone tissue. Immediately after implantation, such an implant has a primary stability that is adequate for fastening the tooth, bridge or prosthesis and for normal use thereof. Promoted by the bioactive surface of the central imlant part, regenerated tissue then successively replaces the resorbable material and grows together with the central implant part. The implant according to the invention thus offers an immediate primary stability without the application of cement and, after a resorption and regeneration phase a permanent secondary stability, which is equal to the stability of known implants. In comparison to known implantation methods, however, there is no transition phase in which, according to the state of the art, the opening 41 is closed and one waits for regeneration of bone tissue before the tooth, the bridge or the prosthesis is fastened directly in the regenerated bone.

Figure 23:
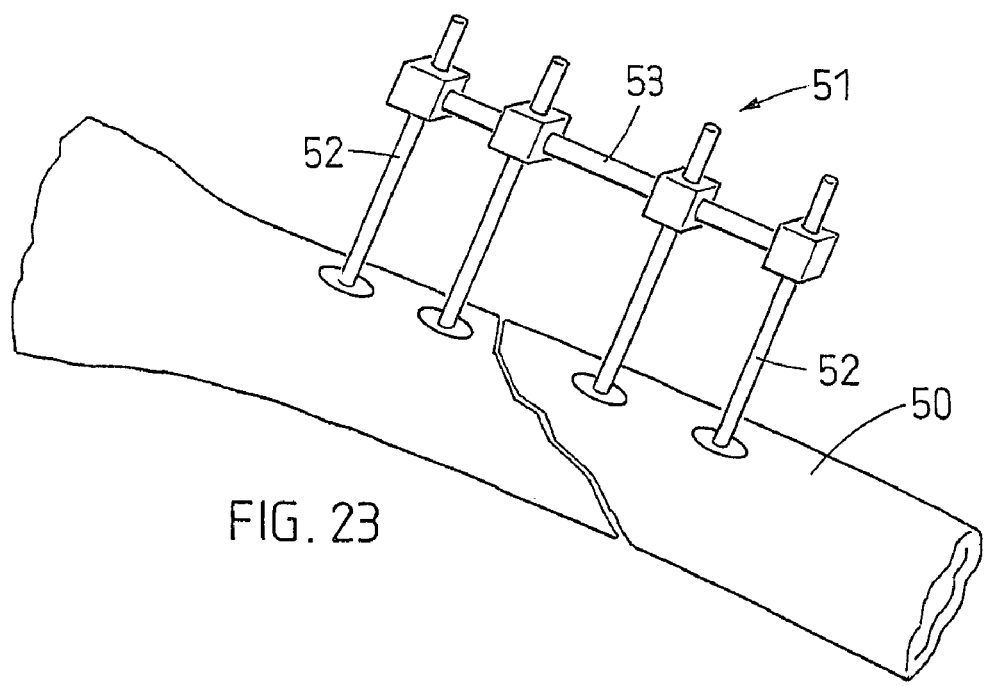
FIG. 23 shows a fixation device fixed to a forearm bone by implants according to the invention.
Figure 24:
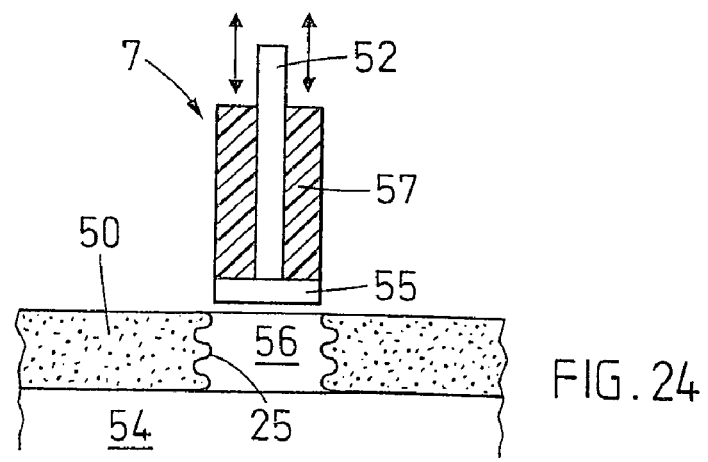
FIG. 24 shows an example of a connection implant suitable for the application as shown in FIG. 23.
Figure 25:
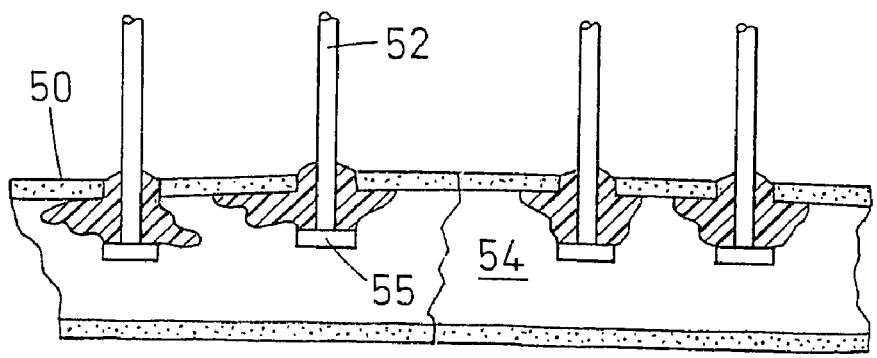
FIG. 25 shows in section the fixation device according to FIG. 23 being fastened on a bone by implants according to FIG. 24.

FIG. 23 shows an external fixation device 51 comprising supports 52 and a carrier 53 fastened on the supports 52, which device is for example fastened on a tubular bone 50 of a human arm according to the invention. The supports 52 are designed as implants according to the invention. The medial part of a tubular bone consists mainly of cortical bone substance and comprises only very little tissue regions that are porous in the context of the invention. For this reason, the marrow space 54 in the inside of the tubular bone 50 is used for the liquefied material to be pressed into. This is shown in FIGS. 24 and 25 in more detail. The supports are provided for example with base plates 55 since the marrow cannot counteract the hydrostatic pressure with sufficient resistance.

In order to fasten the fixation device, openings (with a thread 25 as the case may be) are drilled through the tubular bone 50 extending into the marrow space, wherein the bore diameter corresponds to the diameter of the implant 7 or the base plate 55 respectively. The implant 7 comprises a central support 52, a distal end fastened to the base plate 55, and an annular or tubular region 57 of the liquefiable material arranged around the support and essentially covering the base plate 55. The implant is introduced into the opening 56 and is held at a predefined depth with suitable means to be applied externally. Then the liquefiable material 57 around the support 52 is pressed against the base plate 55 under the effect of ultrasound, so that it is pressed between the bone 50 and the base plate 55 into the marrow space 54 and thus forms a positive-fit connection holding the support 52 in the opening 56. This anchoring permits a unicortical fastening of the support 52, wherein the fastening is secure against tilting. According to the state of the art, such fastening can be achieved only by a bicortical fastening.

Figure 26:
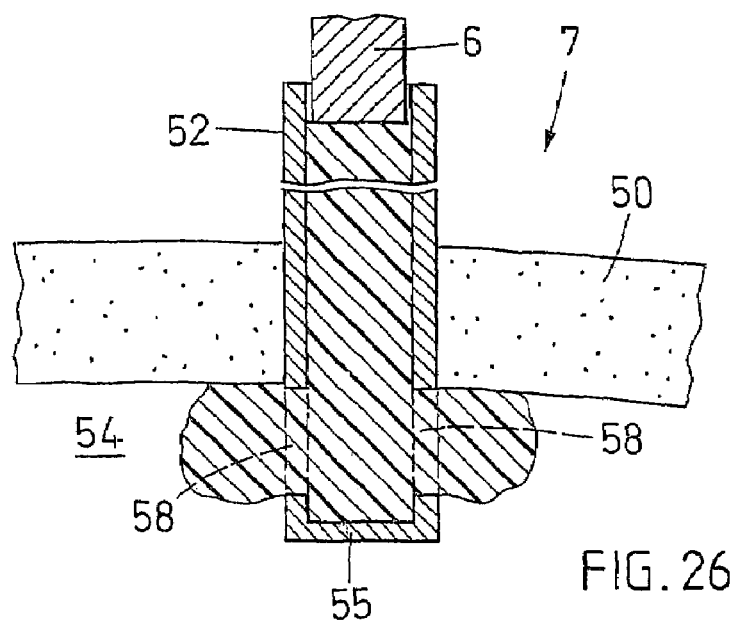
FIG. 26 shows a further example of a connection implant suitable for the application as shown in FIG. 23.

FIG. 26 shows a further embodiment of the implant 7 according to the invention, wherein the is particularly suitable for the application shown in FIG. 23. The liquefiable material, which for example is a thixotropic cement, is arranged in the inside of the support 52, and openings 58 are provided above the base plate 55 and have a size such that the cement cannot exit in its highly viscous form, but exits in its liquefied form by the effect of the resonator 6. The end of the support 52 is designed as a sleeve in the sense of the sleeve according to FIG. 8. The cement pressed through the openings 58 with the help of the resonator secures the support in the marrow cavity, and as the case may be, in the adjacent bone tissue.

Figure 27:
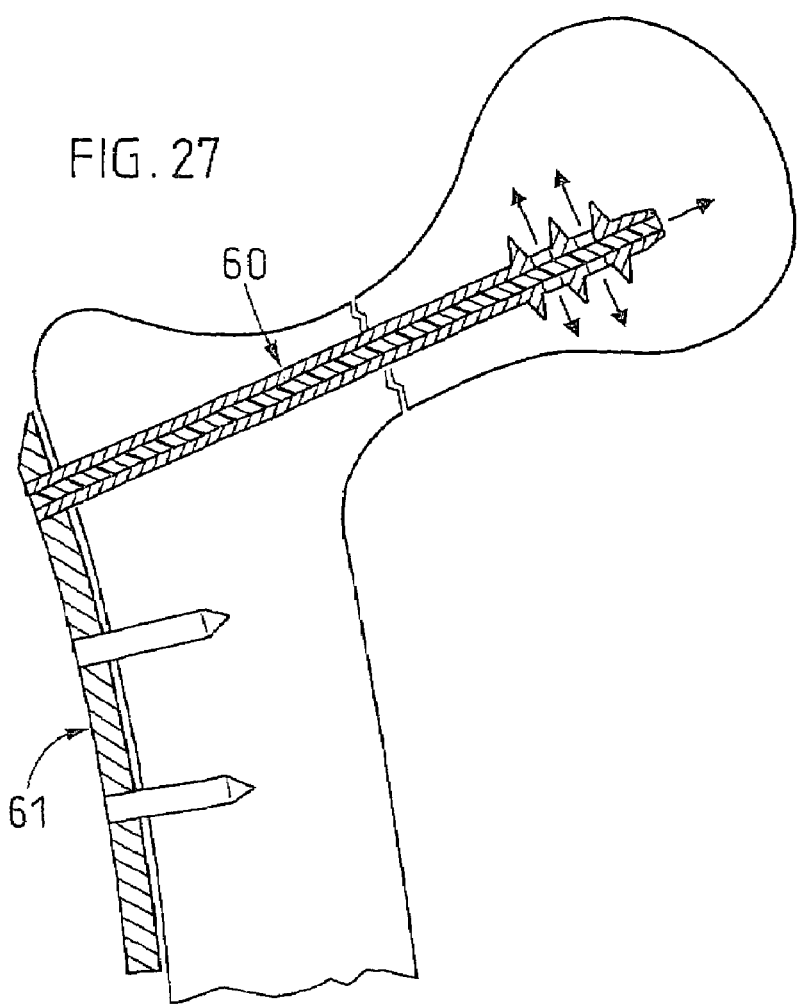
FIG. 27 shows a trochanter plate for fixing a broken neck of a joint, wherein the plate is fixed with the help of an implant according to the invention.

The implant according to the invention shown in FIG. 27 is a tension screw 60, which, for example, is used together with a trochanter plate to fix a broken femoral neck bone. The tension screw 60 (in the sense of an implant sleeve 13, FIG. 8) is hollow and at least in its distal end comprises openings through which a liquefied material can be pressed out in order to anchor this distal region better in osteoporotic bone tissue than is possible alone with the thread of the tension screw. The thread of the screw thus serves in particular for pulling together the tissue in the region of the fracture, until the distal screw end is anchored in the tissue by the liquefiable material.

Figure 28:
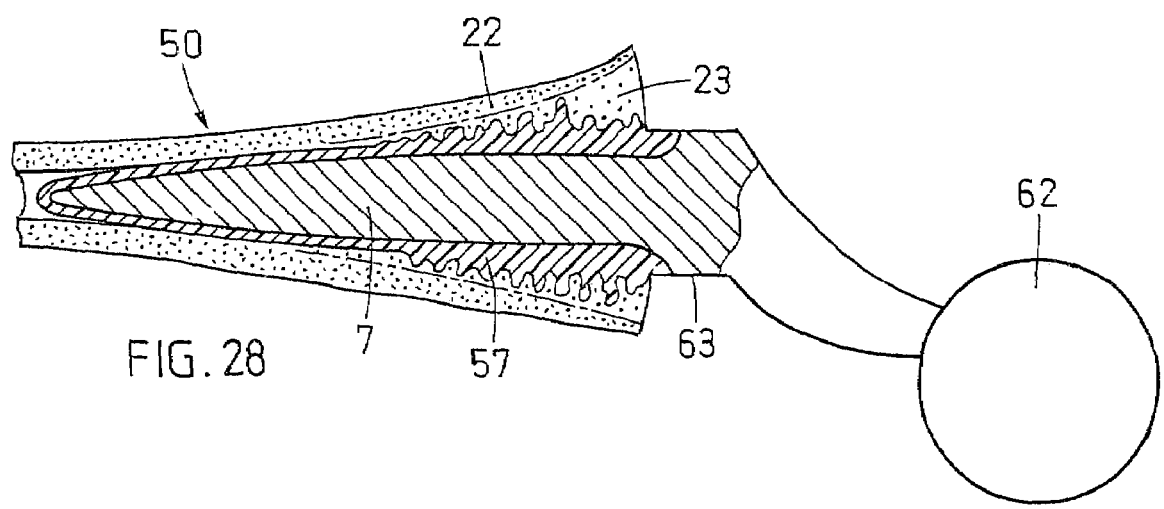
FIG. 28 shows a stem for an artificial joint ball, wherein the stem is fastened to a tubular bone with an implant according to the invention.

FIG. 28 shows, in a very schematic sectional representation, a tubular bone 50 on which an artificial joint element 62 is fastened by way of an implant 7 according to the invention. The stem 63 of the joint element 62 and liquefiable material 57 arranged around the stem represent the implant according to the invention, which is pressed into the tubular bone 50 under the effect of ultrasound, wherein the material 57 is liquefied and is pressed into pores of the cancellous bone 23 and into unevennesses of the inner surface of the cortical substance 22 of the tubular bone. The stem 63 has a surface structure which is suitable for a positive fit connection to the liquefiable material 57, in the same manner as shown for plate 36 in FIG. 17.

A particularly advantageous embodiment of the stem 63 consists, for example, of titanium and has a porous surface that is thus bioactive and it is surrounded by resorbable liquefiable material. Such an implant has a primary stability directly after implantation, which permits at least partial loading. The primary stability is later taken over by a secondary stability effected by the intergrowth of vital bone tissue into the porous surface of the titanium stem 63. This means that the artificial joint element may be loaded essentially immediately after implantation, but without the use of cement. This early loading favors regeneration of the vital tissue and prevents atrophy (osteoporosis). All the same, in a further phase, vital tissue intergrows with the titanium stem.

Figure 29:
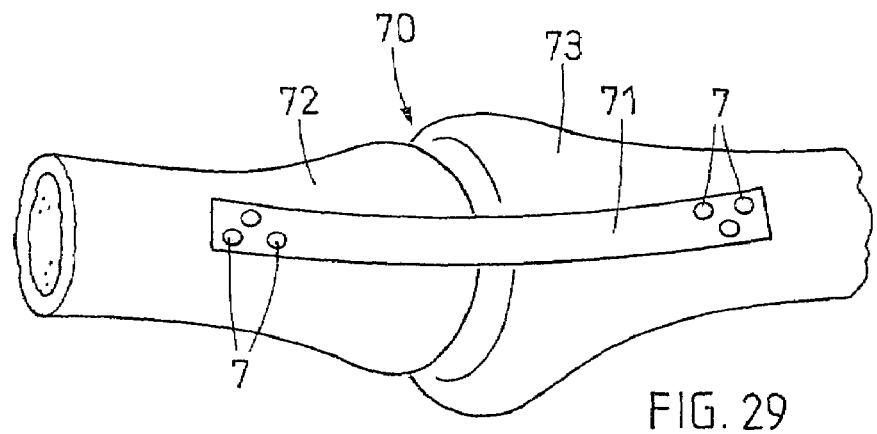
FIG. 29 shows a joint ligament being fastened to bones by implants according to the invention.

FIG. 29 likewise very schematically shows a joint 70 in the region of which a ligament 71 connects the bones 72 and 73. The ligament 71 is naturally intergrown with the bone, wherein this connection may tear on overloading. Implants 7 according to the invention can be used for the repair, wherein implant embodiments according to FIGS. 2 to 4 may be used. For the repair, the cortical substance of the joint bone is opened and pin-like implants 7 are driven through the ligament 71 and secured externally with a head (e.g. according to FIG. 13). Embodiments with less depth effectiveness according to FIGS. 16 and 17 are also conceivable.

Figure 30:
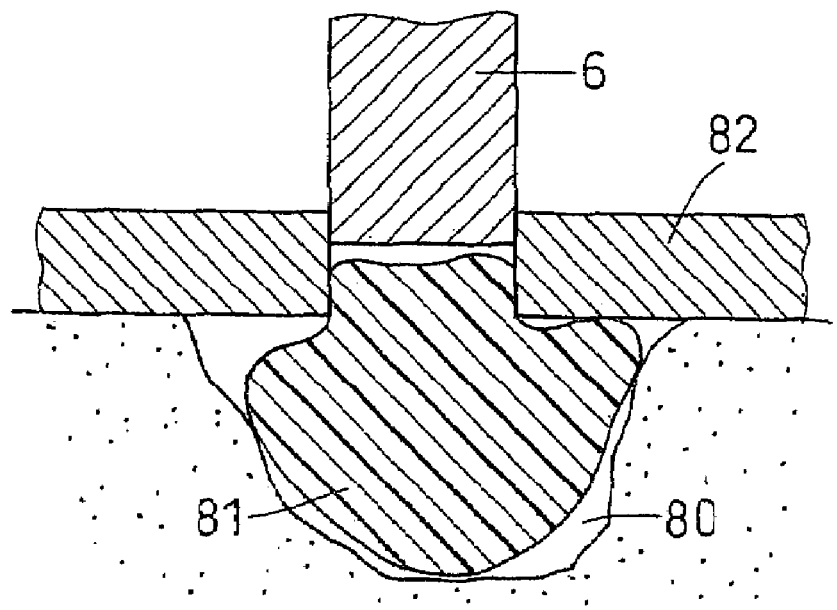
FIG. 30 shows a section through a tissue cavity, for example caused by a tumor, wherein the cavity is to be filled with an implant according to the invention.
Figure 30:
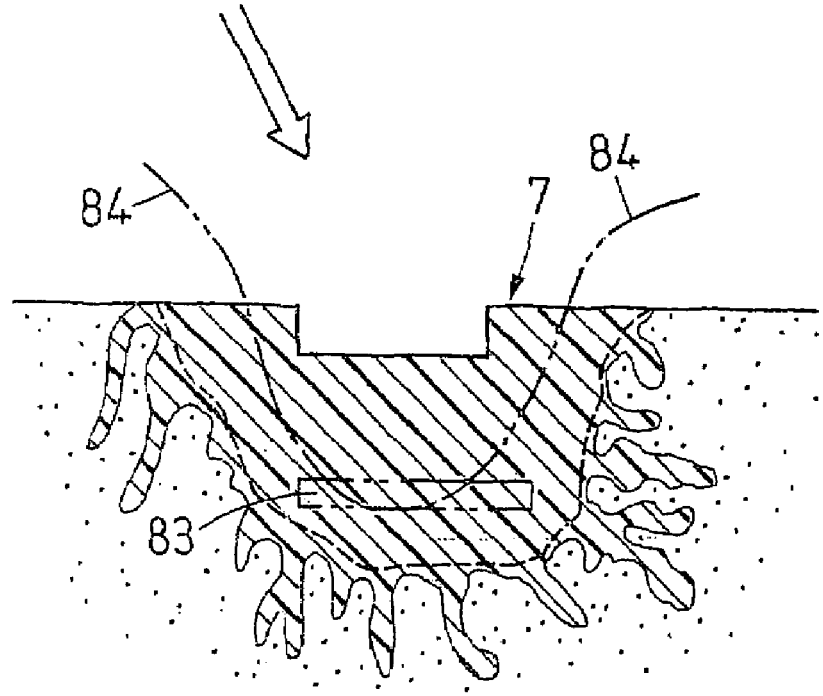

Concluding, FIG. 30 shows that the connection to be created with the implant 7 according to the invention need not necessarily serve the connection of two elements (two tissue parts or a tissue part and an artificial part). It is also conceivable to use an implant according to the invention for filling a tissue opening 80 being caused by a tumour for example. For such an application, an implant 7 of a highly viscous and thixotropic material 81 is used. With the aid of a guide 82 being positioned around the opening, this material is introduced into the opening 18 such that it projects beyond the opening. The resonator 6 used for this application has a cross section corresponding to the inner cross section of the guide 82 and presses the material 81 into the opening 80 like a piston. The opening 80 is thereby not only filled essentially without interstices, but the material 81 becoming liquid under the effect of ultrasound is also pressed into the tissue pores opening into the opening 80, and thereby forms a positive fit connection after solidification, which is shown below in FIG. 30. This positive-fit connection securely holds the implant 7 in its opening 80 even without the opening comprising undercuts, and without providing other retaining means (e.g. periosteum sutured above the implant).

Suitably, finely processed bone material of the patient may be admixed to the liquefiable material.

If in a case as shown in FIG. 30 a thermoplastic material is used instead of the thixotropic cement, the opening 80 may also be specially manufactured for accommodating a fixation element for a wire 84 or suture, as shown dot-dashed in FIG. 30 (only below). A therapeutic auxiliary device, such as a stimulator, may be fixed in the same manner.

EXAMPLE 1

Pins of PLLA and polycarbonate manufactured by injection molding and having a round cross section of diameters between 3.5 and 4.25 mm, a length of 26 to 40 mm (ideal length at 20 kHz: 35 mm), obtusely tapered, distal ends and four grooves axially extending over 10 mm from the distal end were anchored with an excitation frequency of 20 kHz in cancellous bone (femur head) of freshly slaughtered cattle. For implantation, the thin cortical substance layer lying over the cancellous bone was opened, but the cancellous bone was not pre-drilled. On implantation, the implants were pressed against the tissue with pressures of 60 to 130 N and excited with the excitation frequency (sonotrode amplitude approx. 20 to 25 µm). The advance was limited to 10 mm which was achieved in less than 2 s. The implants were then held without excitation for 5 seconds.

The resulting anchorage depths were in the order of 15 mm and the anchorage on tearing out proved to be stronger than the implants themselves (maximum tear-out forces over 500 N). Sensors being placed at 1 mm from the pre-bore in the cortical bone substance (1.5 mm below the bone surface) recorded temperatures of max. 44° C. (approx. 22° above room temperature) approx. 10 s after implantation. The temperature rise was reduced to half its value in approximately 30 seconds.

No molecular weight reduction was found in the implanted PLLA material when compared with the material before implantation.

The invention claimed is:

1. A method for creating a positive-fit connection capable of load-bearing to a tissue part in a human or animal body, the method comprising the steps of:
   providing an implant comprising a biocompatible material being liquefiable by mechanical oscillation,
   positioning the implant on the tissue part in a manner such that an implant region of the liquefiable material is in contact or can be brought into contact with the tissue part,
   impinging the positioned implant with mechanical oscillation and simultaneously pressing the implant against the tissue part for a time sufficient for liquefying at least a part of the liquefiable material and for pressing it into surface unevennesses, cavities or pores of the tissue part and
   letting the liquefiable material pressed into said surface unevennesses, cavities or pores to re-solidify and, in a re-solidified state to constitute the positive-fit connection.

2. The method according to claim 1, wherein the mechanical oscillation for impinging the implant has a predominantly same direction as the pressing of the implant against the tissue.

3. The method according to claim 1, wherein the step of impinging and simultaneous pressing comprises contacting the implant with a transition element which is actively coupled to a resonator of an implantation device, wherein a distal end of the transition element oscillates predominantly perpendicularly to the direction in which the implant is pressed against the tissue part.

4. The method according to claim 1, wherein the step of impinging and simultaneous pressing comprises creating the surface unevennesses, cavities or pores in the tissue part by hydrostatic pressure.

5. The method according to claim 1, and further comprising a step of mechanically creating the surface unevennesses, cavities or pores in the tissue part.

6. The method according to claim 1, wherein the step of letting the liquefiable material to re-solidify comprises stopping the mechanical oscillation, while still pressing the implant against the tissue part.

7. The method according to claim 1, wherein the mechanical oscillation has a frequency of between 2 and 200 kHz.

8. The method according to claim 1, wherein the step of impinging and simultaneous pressing comprises contacting the implant with a resonator of an implantation device.

9. The method according to claim 8, wherein
   the implantation device comprises a generator, an oscillation element and a resonator, the generator being designed for exciting the oscillation element into mechanical oscillation, the resonator and the oscillation element being connected to form an oscillation unit, and a distal end of the resonator being adapted to a proximal face of the implant for transmission of the mechanical oscillations from the resonator to the implant and for pressing the implant against the tissue part.

10. The method according to claim 9, wherein the distal end of the resonator or a distal resonator part is equipped for predominantly oscillating in a longitudinal direction and to press the implant against the tissue part in the same direction.

11. The method according to claim 9, wherein the resonator comprises a transition element which is actively coupled to the resonator, wherein a distal end of the transition element is equipped for predominantly oscillating perpendicularly to a longitudinal direction and to press the implant against the tissue part in the longitudinal direction.

12. The method according to claim 9, wherein the implantation device is designed for mechanical oscillations of the resonator with a frequency between 2 and 200 kHz.

13. The method according to claim 9, wherein the implantation device is designed for a distal end of the resonator to oscillate with an amplitude of between 1 and 100 µm.

14. The method according to claim 9, wherein the oscillation element is a piezoelectric or magnetostrictive oscillator.

15. The method according to claim 9, wherein the implantation device is equipped for setting various frequencies of the mechanical oscillations, various frequency patterns and/or various energy pulsations and wherein the kit further comprises setting instructions for different ones of the implants.

16. The method according to claim 9, wherein the resonator of the implantation device comprises a proximal part and a distal part, the distal part being exchangeably fixed to the proximal part.

17. The method according to claim 1, wherein the step of positioning and the step of impinging and simultaneous pressing comprise minimal invasive surgery.

18. The method according to claim 1, wherein the step of impinging and simultaneous pressing further comprises dissipating heat through a cooling fluid or a heat conducting element.

19. The method according to claim 1, wherein the tissue part comprises living tissue.

20. The method according to claim 1, wherein the tissue part is a human or animal bone part, cartilage part, ligament part or tendon part.

21. The method according to claim 1, and further comprising a step of connecting another tissue part, a suture, a cerclage wire, means for supporting or replacing a tissue part, or a therapeutic auxiliary device to the implant.

22. The method according to claim 1, wherein the tissue part comprises cancellous bone tissue and the liquefiable material is pressed into pores of the cancellous bone tissue.

23. The method according to claim 22, wherein the cancellous bone tissue is osteoporotic bone tissue and is fortified by the liquefiable material pressed into the pores.

24. The method according to claim 1, wherein the implant further comprises a proximal face suitable for transmission of mechanical oscillation into the implant and for simultaneously pressing the implant against the tissue part and a contact surface to be brought into contact with the tissue part, wherein the liquefiable material is arranged to be liquefied by the mechanical oscillation on the contact surface or in a position from which it can be pressed onto the contact surface.

25. The method according to claim 24, wherein the liquefiable material has thermoplastic or thixotropic properties.

26. The method according to claim 1, wherein the liquefiable material is at least partly resorbable.

27. The method according to claim 1, wherein the liquefiable material further comprises foreign phases or substances having further functions.

28. The method according to claim 1, wherein the implant is designed to be suitable as an anchoring means for an artificial support or fixation element, for a prosthesis of a joint ball or socket, for an artificial tooth, bridge or tooth prosthesis, for a suture thread, for a cerclage wire or for a therapeutic auxiliary device.

29. The method according to claim 1, wherein the implant comprises a sleeve (13) of a non-liquefiable material wherein the liquefieable material is arranged in an inside of the sleeve wherein the sleeve comprises opening (58) for exit of the liquefied material and wherein in the step of impinging and simultaneously pressing, a distal end of a resonator is positioned against a proximal face of the liquefiable material.

30. The method according to claim 29, wherein the liquefiable material is resorbable and the sleeve (13) at least partly has a bioactive surface.

31. The method according to claim 29, wherein the implant is a screw and the step of positioning comprises screwing the implant into bone tissue.

32. The method according to claim 31, wherein the implant is a tension screw and is used together with a trochanter plate for fixing a fractured femoral neck bone.

33. The method according to claim 1, wherein the implant is shaped as a plate (35 and 36) or film (35).

34. The method according to claim 33, wherein the plate or film (35) is of one layer.

35. The method according to claim 33, wherein the plate (35 and 36) or film comprises a layer of the liquefiable material and a layer of a non-liquefiable material, and wherein the liquefiable material covers at least a part of one surface of the non-liquefiable material, and wherein the liquefiable material layer and the non-liquefiable material layer are connected to one another by positive fit or material fit.

36. The method according to claim 33, wherein the implant is positioned over a bone fracture or across a gap between two bone plates or between a bone plate and an artificial plate replacing a bone plate and wherein the step of impinging and simultaneously pressing is carried out on both sides of the fracture or gap.

37. A method for creating a positive-fit connection capable of load-bearing to a tissue part in a human or animal body, the method comprising the steps of:

providing a pin- or dowel-shaped implant comprising a proximal face, a contact surface to be brought into contact with the tissue part, and a first material being biocompatible, having thermoplastic properties, and being liquefiable by mechanical oscillation, the first material constituting at least part of the contact surface, positioning the implant on the tissue part in a manner such that at least part of the contact surface is in contact with the tissue part, impinging the proximal face of the positioned implant with mechanical oscillation and simultaneously pressing the implant against the tissue part for a time sufficient for liquefying at least part of the liquefiable material in contact with the tissue part and for pressing it into surface unevennesses, cavities or pores of the tissue part, and letting the liquefiable material pressed into said surface unevennesses, cavities or pores to re-solidify and, in a re-solidified state, to constitute the positive-fit connection.

38. The method according to claim 37, wherein the mechanical oscillation for impinging the implant has a predominantly same direction as the pressing of the implant against the tissue part.

39. The method according to claim 37, wherein the step of impinging and simultaneous pressing comprises contacting the implant with a transition element which is actively coupled to a resonator of an implantation device, wherein a distal end of the transition element oscillates predominantly perpendicularly to the direction in which the implant is pressed against the tissue part.

40. The method according to claim 37, wherein the step of impinging and simultaneous pressing comprises creating the surface unevennesses, cavities or pores in the tissue part by hydrostatic pressure.

41. The method according to claim 37, and further comprising a step of mechanically creating the surface unevennesses, cavities or pores in the tissue part.

42. The method according to claim 37, wherein the step of letting the liquefiable material to re-solidify comprises stopping the mechanical oscillation, while still pressing the implant against the tissue part.

43. The method according to claim 37, wherein the mechanical oscillation has a frequency of between 2 and 200 kHz.

44. The method according to claim 37, wherein the step of impinging and simultaneous pressing comprises pressing with a force of 0.5 to 5 N per mm2 of implant cross section.

45. The method according to claim 37, wherein the step of positioning and simultaneous pressing comprises minimal invasive surgery.

46. The method according to claim 37, wherein the step of impinging and simultaneous pressing comprises dissipating heat from the implantation site through a cooling fluid or a heat conducting element.

47. The method according to claim 37, wherein the tissue part comprises living tissue.

48. The method according to claim 37, wherein said tissue part is a human or animal bone part, cartilage part, ligament part or tendon part.

49. The method according to claim 37, and further comprising a step of connecting another tissue part, a means for supporting or replacing a tissue part, a suture, a cerclage wire, or a therapeutic auxiliary device to the implant.

50. The method according to claim 37, and further comprising a step of providing an opening in the tissue part, wherein the step of positioning comprises positioning the implant in the tissue opening.

51. The method according to claim 50, wherein the step of providing an opening in the tissue part comprises drilling the opening.

52. The method according to claim 50, wherein the tissue part is a bone part with an outer layer of cortical bone and inner cancellous bone and wherein the step of providing an opening in the tissue part comprises opening the cortical layer only.

53. The method according to claim 50, wherein the tissue part is a bone part comprising an outer layer of cortical bone, wherein the step of providing an opening comprises opening the cortical layer and wherein surface unevennesses or a surface roughness are created on the walls of the opening in the cortical layer.

54. The method according to claim 53, wherein a thread is created in the walls of the opening in the cortical layer.

55. The method according to claim 50, wherein a cross section of the opening provided in the tissue part is sufficiently smaller than a corresponding cross section of the implant, for achieving a friction-fit between a wall of the opening and the implant.

56. The method according to claim 37, wherein the step of impinging and simultaneous pressing comprises driving the implant into the tissue part to form an opening therein.

57. The method according to claim 37, wherein the step of impinging and simultaneous pressing comprises guiding the implant with the aid of an implant guide.

58. The method according to claim 57, wherein the implant is guided in a tubular guide or with the aid of a guide wire.

59. The method according to claim 37, wherein, for the step of positioning and for the step of impinging and simultaneous pressing, a proximal implant end is fixed to a distal end of a resonator of an implantation device.

60. The method accordinci to claim 59, wherein:
the implantation device comprises a generator, an oscillation element and a resonator, the generator being designed for exciting the oscillation element into mechanical oscillation, the resonator and the oscillation element being connected to form an oscillation unit, and a distal resonator end being adapted to the proximal face of the implant for transmission of the mechanical oscillations from the resonator into the implant and for pressing the implant against the tissue part.

61. The method according to claim 60, wherein the oscillation element is a piezoelectric or magnetostrictive oscillator.

62. The method according to claim 60, wherein the oscillation unit is driven to oscillate with a frequency between 2 and 200 kHz.

63. The method according to claim 60, wherein the resonator comprises a proximal part and a distal part, the distal part being exchangeably fixed to the proximal part.

64. The method according to claim 60, wherein the generator and the oscillation unit are designed for a distal resonator end to oscillate with an amplitude of between 1 and 100 µm.

65. The method according to claim 60, wherein the implantation device further comprises a housing and an implant guide supported on the housing.

66. The method according to claim 65, wherein the implant is a dental implant.

67. The method according to claim 60, wherein the distal end of the of the resonator is equipped for oscillating in a longitudinal direction and to press the implant against the tissue part in the same longitudinal direction.

68. The method according to claim 60, wherein the resonator comprises a transition element which is actively coupled to the resonator, wherein a distal end of the transition element is equipped for predominantly oscillating perpendicularly to a longitudinal direction and to press the implant against the tissue part in the longidtudinal direction.

69. The method according to claim 60, wherein the implantation device is equipped for setting various frequencies of the mechanical oscillations, various frequency patterns and/or various energy pulsations and wherein the kit further comprises setting instructions for different ones of the implants.

70. The method according to claim 60, wherein the resonator comprises a proximal part and a distal part, the distal part being exchangeably fixed to the proximal part.

71. The method according to claim 60, wherein the resonator or a distal part thereof is adapted for minimal invasive surgery.

72. The method according to claim 60, wherein the resonator of the implantation device or a distal part thereof is exchangeable and sterilizeable.

73. The method according to claim 60, wherein a proximal send of the implant and a distal end of the resonator comprise cooperating holding means for the proximal implant end to be able to be held at the distal resonator end.

74. The method according to claim 73, wherein the cooperating holding means comprise elements of a snapclosure, materials suitable to be bonded together, a securing pin, or a threaded bolt.

75. The method according to claim 73, wherein the proximal end of the implant consists of the first material and wherein a distal face of the resonator carries at least one energy director.

76. The method according to claim 60, wherein a distal face of the resonator or of a distal resonator part corresponds in cross section to the proximal face of the implants.

77. The method according to claim 37, wherein, for the step of impinging and simultaneous pressing, a distal end of a resonator of an implantation device is positioned on the proximal face of the implant and acts like a hammer thereon.

78. The method according to claim 77, wherein the proximal face of the implant comprises a second material which is not liquefiable under implantation conditions.

79. The method according to claim 77, wherein the proximal face of the implant comprises the first material and a distal face of the resonator comprises at least one energy director and wherein the method comprises a step of deform ing the proximal face of the implant with the aid of the distal face of the resonator and mechanical oscillation.

80. The method according to claim 79, wherein the step of deforming is carried out before the step of positioning and further comprises bonding the deformed proximal face of the implant to the distal face of the resonator.

81. The method according to claim 77, wherein the implantation device comprises a generator, an oscillation element and a resonator, the generator being designed for exciting the oscillation element into mechanical oscillation, the resonator and the oscillation element being connected to form an oscillation unit, and a distal resonator end being adapted to the proximal face of the implant for transmission of the mechanical oscillations from the resonator into the implant and for pressing the implant against the tissue part.

82. The method according to claim 37, wherein the implant comprises a core of a second material which is not liquefiable under implantation conditions.

83. The method according to claim 82, wherein the core is removed after implantation.

84. The method according to claim 83, wherein the core is a guide wire.

85. The method according to claim 82, wherein the implant is a part of a prosthesis and the step of positioning comprises positioning said prothesis part in bone tissue.

86. The method according to claim 82, wherein the implant is a dental implant and the step of positioning comprises positioning the implant in an opening in a jaw bone.

87. The method according to claim 37, wherein the step of positioning comprises positioning the implant through a tendon or ligament onto bone tissue situated underneath the tendon or ligament or into an opening provided in the bone tissue underneath the tendon or ligament.

88. The method according to claim 37, wherein a further implant which has the shape of a plate is attached to the tissue part with the aid of the implant or with the aid of a plurality of the implants.

89. The method according to claim 88, wherein the plate is fixed to a proximal end of the implant or implants.

90. The method according to claim 88, wherein the plate is a fixation or stabilization plate.

91. The method according to claim 90, wherein the fixation or stabilization plate is positioned across a bone fracture or laceration.

92. The method according to claim 90, wherein the fixation or stabilization plate is positioned in a head region of a patient for repair or reconstruction purposes.

93. The method according to claim 90, wherein the fixation or stabilization plate is positioned across a gap between two calvaria parts or between a calvaria part and an artificial cover plate replacing a calvaria part.

94. The method according to claim 90, wherein the fixation or stabilization plate is positioned over at least two vertebral bodies.

95. The method according to claim 94, wherein the plate is elastically deformable.

96. The method according to claim 88, wherein the plate comprises at least one through opening and, in the step of positioning, the plate is positioned against the tissue part and the implant is positioned through the through opening in the plate onto the tissue part or into an opening provided in the tissue part.

97. The method according to claim 96, wherein the proximal implant end comprises a head having a larger cross section than a cross section of the through opening.

98. The method according to claim 96, wherein the plate consists of a second material, which is not liquefiable under implantation conditions, and the step of impinging and simultaneous pressing comprises pressing the first material into the through opening, which comprises a wall with unevennesses, cavities or pores.

99. The method according to claim 96, wherein the plate consists of a third material having thermoplastic properties and the step of impinging and simultaneous pressing comprises welding or adhering a region of the implant comprising the first material into the opening of the plate.

100. The method according to claim 96, wherein the step of impinging and simultaneous pressing comprises driving the implant into the bone tissue sufficiently for the proximal implant end to be flush with an outer surface of the plate.

101. The method according to claim 37, wherein the implant has a plurality of different cross sections between a distal and a proximal end thereof.

102. The method according to claim 101, comprising steps between different cross sections.

103. The method method according to claim 37, wherein the first material is a non-resorbable or a resorbable polymer.

104. The method according to claim 103, wherein the first material is a polyethylene (PE), a polymethyl metacrylate (PMME), a polycarbonate (PC), a polyamide, a polyester, a polyacrylate, a polymer based on lactic acid and/or glycolic acid, a polyhydroxyalkanoate (PHA), a polycaprolactone (PCL), a polysaccharide, a polydioxanone (PD), a polyanhydride or a corresponding copolymer.

105. The method according to claim 104, wherein the polymer based on lactic acid and/or glycolic acid is PLA, PLLA, PGA, or PLGA.

106. The method according to 37, wherein the first material further contains foreign phases or additional substances suitable for reinforcing, swelling or rendering porous the material, or for promotion of healing or regeneration, or for furthering x-ray visibility.

107. The method according to claim 106, wherein the additional substance is a growth factor, an antibiotic, an inflammation inhibitor or a buffer.

108. The method according to claim 106, wherein the foreign phases are fibers or whiskers.

109. The method according to claim 37, wherein implant surfaces of the first material are equipped with energy directors in the form of projecting pyramids, cones, hemispheres or ribs.

110. The method according to claim 37, wherein implant surfaces of the first material comprise axially extending ribs which constitute humps or corners of an implant cross section.

111. The method according to claim 37, wherein the distal implant end is pointed or tapers to a plurality of point-like or linear tip regions.

112. The method according to claim 37, wherein the first material constitutes the whole implant.

113. The method according to claim 37, wherein the implant comprises a core with a proximal end, a distal end and a circumferential surface between the proximal end and the distal end and consisting of a second material which is not liquefiable at implantation conditions, and wherein the first material is arranged on the distal end of the core and/or on the circumferential surface of the core.

114. The method according to claim 113, wherein the second material of the core is a metal, a ceramic material, a glass, a polymer or a composite material.

115. The method according to claim 113, wherein the second material comprises titanium, a cobalt-chrome alloy, polyetheraryl ketone, polyfluoro- and/or polychloroethylene, polyetherimide, polyethersulphone, polyvinylchloride, polyurethane, polysulphone, polyester, aluminium oxide, zirconium oxide, a silicate, a calcium phosphate ceramic or glass, or a carbon fiber reinforced high-temperature thermoplastic polymer.

116. The method according to claim 113, wherein the first material is resorbable and the core comprises a bioactive surface.

117. The method according to claim 113, wherein the core is a stem of a joint prosthesis.

118. The method according to claim 113, wherein the implant is a dental implant to be implanted in a jaw bone.

119. The method according to claim 37, wherein a proximal implant end comprises a head.

120. The method according to claim 37, wherein the implant is designed for replacing a further tissue part or for fastening a further tissue part, a therapeutic auxiliary device, a suture, a cerclage wire, an artificial support or fixation element, an artificial joint socket or ball, or an artificial tooth, bridge or tooth prosthesis.

121. The method according to claim 37, wherein, for being held by a distal end of a resonator, a proximal end of the implant is equipped with an inner thread, a resilient head or a through bore.

122. The method according to claim 37, wherein the connection to be created is a pointwise, depth-effective connection.

123. The method according to claim 37, wherein the connection to be created is a large-surfaced, superficial connection.

124. The method according to claim 123, wherein suitable tissue surface regions are roughened before positioning the implant (7).

* * * * *

UNITED STATES PATENT AND TRADEMARK OFFICE
CERTIFICATE OF CORRECTION

| | | |
|---|---|---|
| PATENT NO. | : 7,335,205 B2 | Page 1 of 1 |
| APPLICATION NO. | : 10/415454 | |
| DATED | : February 26, 2008 | |
| INVENTOR(S) | : Aeschlimann et al. | |

It is certified that error appears in the above-identified patent and that said Letters Patent is hereby corrected as shown below:

In Column 21, Line 27 (Claim 60, Line 1), delete "accordinci" and insert --according--.

In Column 22, Line 11 (Claim 73, Line 2), delete "send" and insert --end--.

Signed and Sealed this

Nineteenth Day of August, 2008

JON W. DUDAS
*Director of the United States Patent and Trademark Office*